United States Patent
Chiang et al.

(10) Patent No.: US 10,458,893 B2
(45) Date of Patent: Oct. 29, 2019

(54) MINIATURIZED PARTICULATE MATTER DETECTOR AND MANUFACTURING METHOD OF A FILTER

(71) Applicant: Industrial Technology Research Institute, Hsinchu (TW)

(72) Inventors: Chia-Wen Chiang, Taichung (TW); Cheng-Ta Ko, Taipei (TW); I-Hsing Lin, Hsinchu (TW); Hsiang-Hung Chang, Hsinchu County (TW); Wen-Chih Chen, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 385 days.

(21) Appl. No.: 15/245,199

(22) Filed: Aug. 24, 2016

(65) Prior Publication Data

US 2017/0052103 A1 Feb. 23, 2017

Related U.S. Application Data

(63) Continuation-in-part of application No. 14/953,424, filed on Nov. 30, 2015, now Pat. No. 10,121,673.

(30) Foreign Application Priority Data

Aug. 19, 2015 (TW) .............................. 104127014 A
Jun. 29, 2016 (TW) .............................. 105120516 A

(51) Int. Cl.
*G01N 15/06* (2006.01)
*G01N 15/00* (2006.01)

(52) U.S. Cl.
CPC . *G01N 15/0656* (2013.01); *G01N 2015/0046* (2013.01)

(58) Field of Classification Search
CPC ............. G01N 15/0656; G01N 1/2205; G01N 15/0606; G01N 15/0272; G01N 5/02; G01N 2015/0046
See application file for complete search history.

(56) References Cited

U.S. PATENT DOCUMENTS

| | | |
|---|---|---|
| 5,060,508 A | 10/1991 | Wong |
| 5,932,795 A | 8/1999 | Koutrakis et al. |

(Continued)

FOREIGN PATENT DOCUMENTS

| | | |
|---|---|---|
| CN | 1075549 | 8/1993 |
| CN | 1120668 | 4/1996 |

(Continued)

OTHER PUBLICATIONS

"Office Action of U.S. Appl. No. 14/953,424", dated Dec. 14, 2017, p. 1-p. 29.

(Continued)

*Primary Examiner* — Justin Seo
*Assistant Examiner* — John M Royston
(74) *Attorney, Agent, or Firm* — JCIPRNET

(57) ABSTRACT

A miniaturized particulate matter detector that includes a filter and a concentration detector is provided. The filter has a plurality of holes, and the concentration detector is correspondingly disposed under the filter. The concentration detector has a detected area used to detect a concentration of at least one miniaturized particulate matter. A manufacturing method of the filter is also provided.

14 Claims, 19 Drawing Sheets

(56) References Cited

U.S. PATENT DOCUMENTS

| | | | |
|---|---|---|---|
| 6,750,449 B2 | 6/2004 | Marcus | |
| 6,964,190 B2 | 11/2005 | Shinohara et al. | |
| 7,100,423 B2 | 9/2006 | Trenholm | |
| 7,168,292 B2 | 1/2007 | Gundel et al. | |
| 7,254,212 B2 | 8/2007 | Saitoh et al. | |
| 7,325,465 B2 | 2/2008 | Solomon et al. | |
| 7,377,187 B2 | 5/2008 | Lai et al. | |
| 8,225,684 B2 | 7/2012 | Kondo et al. | |
| 8,534,116 B2 | 9/2013 | Wang et al. | |
| 2005/0188746 A1 | 9/2005 | Shinohara et al. | |
| 2008/0105034 A1 | 5/2008 | Parfitt et al. | |
| 2009/0314066 A1 | 12/2009 | Nieuwenhuis et al. | |
| 2010/0043527 A1* | 2/2010 | Marra | B60H 1/008 73/28.02 |
| 2012/0208283 A1 | 8/2012 | Gheorghiu et al. | |
| 2012/0244037 A1 | 9/2012 | Matsumoto et al. | |
| 2013/0056367 A1* | 3/2013 | Martinez | G01N 27/4146 205/792 |
| 2013/0213115 A1 | 8/2013 | Chu et al. | |
| 2014/0083167 A1 | 3/2014 | Liu et al. | |
| 2016/0063833 A1* | 3/2016 | Schultz | G08B 19/00 340/522 |

FOREIGN PATENT DOCUMENTS

| | | |
|---|---|---|
| CN | 1314996 | 9/2001 |
| CN | 200941093 | 8/2007 |
| CN | 100464060 | 2/2009 |
| CN | 101793666 | 8/2010 |
| CN | 201637649 | 11/2010 |
| CN | 101983098 | 3/2011 |
| CN | 102224406 | 10/2011 |
| CN | 102590088 | 7/2012 |
| CN | 103403538 | 11/2013 |
| CN | 103674793 | 3/2014 |
| CN | 103765191 | 4/2014 |
| CN | 103940711 | 7/2014 |
| CN | 103940711 A * | 7/2014 |
| CN | 104568684 | 4/2015 |
| TW | 363178 | 7/1999 |
| TW | 200528179 | 9/2005 |
| TW | 200730814 | 8/2007 |
| TW | 201027060 | 7/2010 |

OTHER PUBLICATIONS

Office Action of China Counterpart Application, dated Sep. 27, 2018, pp. 1-9.

"Office Action of Taiwan Counterpart Application", dated Feb. 8, 2017, p. 1-p. 10.

Mehdizadeh et al., "A two-stage aerosol impactor with embedded MEMS resonant mass balances for particulate size segregation and mass concentration monitoring," IEEE Sensors, Nov. 3-6, 2013, pp. 1-4.

Hajjam et al., "Thermally actuated MEMS resonant sensors for mass measurement of micro/nanoscale aerosol particles," IEEE Sensors, Oct. 25-28, 2009, pp. 707-710.

Budde et al., "Enabling Low-Cost Particulate Matter Measurement for Participatory Sensing Scenarios," Proceedings of the 12th International Conference on Mobile and Ubiquitous Multimedia, Dec. 2, 2013, pp. 1-10, article No. 19.

Budde et al., "Investigating the use of commodity dust sensors for the embedded measurement of particulate matter," 9th International Conference on Networked Sensing Systems (INSS), Jun. 11-14, 2012, pp. 1-4.

Yuen et al., "Microfluidic-based real-time detector for fine particulate matter," IEEE Sensors, Nov. 2-5, 2014, pp. 775-778.

* cited by examiner

MINIATURIZED PARTICULATE MATTER DETECTOR AND MANUFACTURING METHOD OF A FILTER

CROSS-REFERENCE TO RELATED APPLICATION

This application is a continuation-in-part application of and claims the priority benefit of an application Ser. No. 14/953,424, filed on Nov. 30, 2015, now pending, which claims the priority benefit of Taiwan application serial no. 104127014, filed on Aug. 19, 2015. This application also claims the priority benefit of Taiwan application serial no. 105120516, filed on Jun. 29, 2016. The entirety of each of the above-mentioned patent applications is hereby incorporated by reference herein.

TECHNICAL FIELD

The disclosure relates to a miniaturized particulate matter detector and a manufacturing method of a filter.

BACKGROUND

According to World Health Organization's prediction, death rate of lung cancer may be ranking up to fifth class in the world. Currently, lung cancer is detected by the X-ray machine. However, it is discovered usually in the lung cancer last stage. Except smoking, the reasons causing the lung cancer further include particulate matters of air pollution.

Traditional monitors for detecting particulate matter concentration have a huge volume, for example, the weighing measurement machine is continuously collecting the particulate matters in the air for 24 hours, and placing the collected particulate matters on the filter paper for measuring the weight of the particulate matters, and then converting the measured weight value into the concentration value.

Cyclone-type miniaturized particulate matter filter is used to fix the air speed and select an exact size of miniaturized particulate matter. The filter has problems of huge volume and regularly cleaning to maintain the fixed air speed. Impactor-type miniaturized particulate matter filter collects the miniaturized particulate matters from the air that passes through a numbers of large, medium, and small sizes of holes as well as a blocking plate under the holes. Cyclone-design miniaturized particulate matter filter also uses the cyclone-type scheme to collect miniaturized particulate matters. Other schemes of collecting miniaturized particulate matters include C14 measurement, optical measurement, Tape Element Oscillator Measurement (TEOM), and so on. Their principles are selecting exact miniaturized particulate matters and proceeding a mass measurement.

SUMMARY

An embodiment of the disclosure provides a miniaturized particulate matter detector. The miniaturized particulate matter detector comprises a filter having a plurality of holes and a concentration detector that is correspondingly disposed under the filter. The concentration detector has a detect area used for detecting a concentration of at least one miniaturized particulate matter.

Another embodiment of the disclosure provides a manufacturing method of a filter. The manufacturing method comprises: providing a substrate; coating or lithographic printing a photoresist material on the substrate; etching a plurality of openings on the substrate, wherein the plurality of openings have an opening shape of gradually reducing, or gradually expanding or cylindrical; removing the photoresist material from the substrate; pasting a support plate on a surface of the plurality of openings on the substrate; grinding the substrate until to expose the plurality of openings to form a plurality of through-silicon vias (TSVs); and cutting off the substrate and including the plurality of TSVs.

Another embodiment of the disclosure provides a miniaturized particulate matter detector. The miniaturized particulate matter detector comprises a filter, a concentration detector, a first electrode, and a second electrode. The filter has a plurality of holes. The concentration detector is correspondingly disposed under the filter and has a detect area. The first electrode has a plurality of discharge tips pointing at the concentration detector, and the plurality of discharge tips are suitable for charging the particulate matter. The concentration detector is located between the first electrode and the second electrode that are adapted to generate an electric field at least applied between the filter and the concentration detector, so as to drive the charged particulate matter toward the concentration detector from the filter. The charged particulate matter is then attached to the detect area of the concentration detector.

The foregoing will become better understood from a careful reading of a detailed description provided herein below with appropriate reference to the accompanying drawings.

DETAILED DESCRIPTION OF DISCLOSED EMBODIMENTS

Figure 1A:
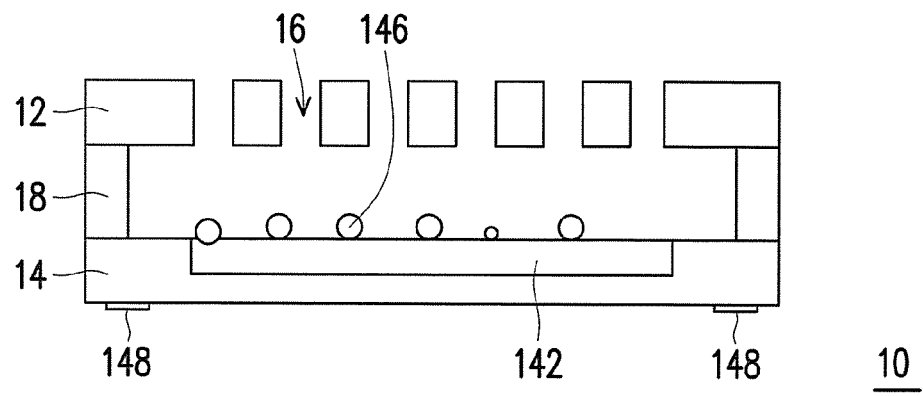
FIG. 1A is a cross-sectional schematic view of a miniaturized particulate matter detector according to a first exemplary embodiment.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

The disclosure relates to a miniaturized particulate matter detector and a manufacturing method of a filter suitable for miniaturization.

The miniaturized particulate matter detector provided in the exemplary embodiments uses the developer and the etching scheme to make the TSV filter, and this may greatly reduce the selecting number of the opening size and the inlet sizes for detecting the miniaturized particulate matter. Arrangement of a modularized detector, for instance, a MEMS oscillator or a quartz oscillator may miniaturize these modules. The replaceable function allows the replacement of the filter that has no filtering function or the replacement of the detector that is supersaturated. Mass production and assembly in batch reduce the costs. Besides, modularized products may be applied in portable products, for example, cell phones.

FIG. 1A is a cross-sectional schematic view of a miniaturized particulate matter detector according to a first exemplary embodiment. With reference to FIG. 1A, the miniaturized particulate matter detector 10 comprises a filter 12 and a concentration detector 14. The filter 12 has a plurality of holes 16, and the concentration detector 14 is correspondingly disposed under the filter 12. The concentration detector 14 has a detect area 142 used to detect a concentration of at least one miniaturized particulate matter. In an embodiment, the opening shape of the holes 16 may be a cylindrical. The holes may be TSVs (Through Silicon Vias). In an embodiment, an adhesive material 18 may be disposed between the concentration detector 14 and the filter 12 to seal or bonding the concentration detector 14 and the filter 12 at two closer edges of the concentration detector 14 and the filter 12.

Figure 1B:
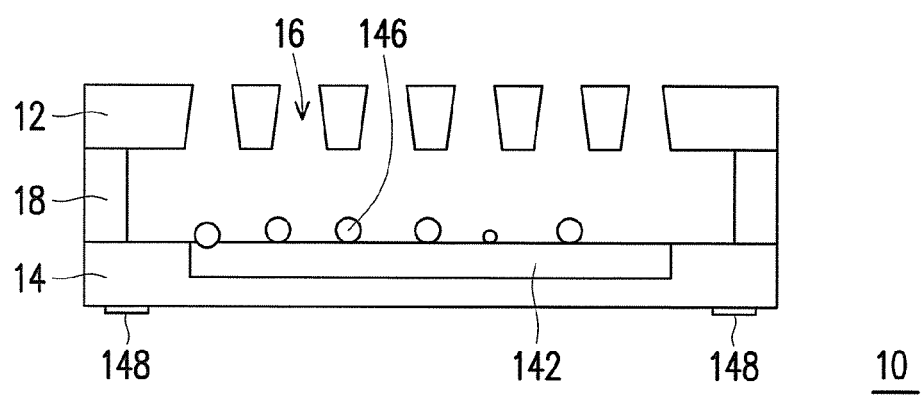
FIG. 1B is a cross-sectional schematic view of a miniaturized particulate matter detector according to a second exemplary embodiment.

FIG. 1B is a cross-sectional schematic view of a miniaturized particulate matter detector according to a second exemplary embodiment. Please refer to FIG. 1B, the structure of the miniaturized particulate matter detector in FIG. 1B is same as that in the first embodiment of FIG. 1A. The difference is the opening shape of all or part of holes 16 may be a gradually reducing shape or a gradually expanding shape. The holes 16 may be, but not limited to TSVs. Herein, the gradually reducing shape of one hole 16 is defined as a cross-sectional area of a first end (entrance end) of the hole 16 is larger than that of a second end (exit end) of the hole 16. Namely, the area of an inlet (second end) of the hole 16 is smaller than that of an outlet (first end) of the hole 16. The gradually expanding shape is defined as a cross-sectional area of a first end of the hole 16 is larger than that of a second end of the hole 16. Namely, the area of an inlet (first end) is smaller than that of an outlet (second end). In one embodiment, all or part of the plurality of holes 16 of the filter 12 may have an opening shape of the gradually reducing shape or the gradually expanding shape. The gradually reducing shape or the gradually expanding shape of the holes 16 may be regular or irregular, or the opening shape of the plurality of holes may be fixed and is the cylindrical.

Figure 1C:
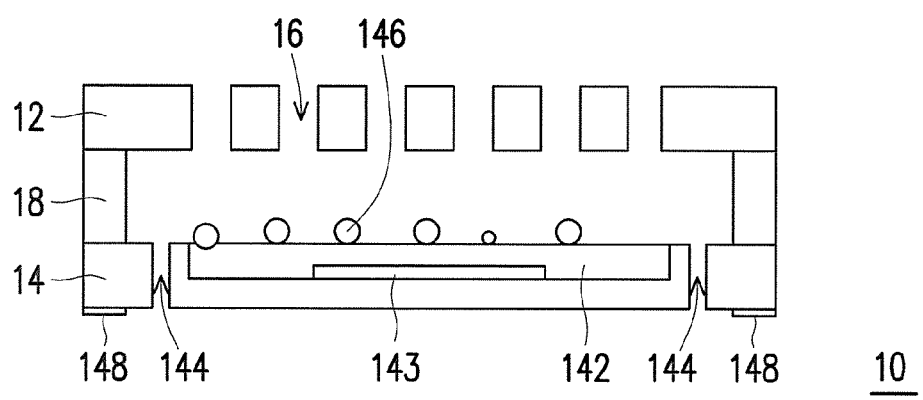
FIG. 1C is a cross-sectional schematic view of a miniaturized particulate matter detector according to a third exemplary embodiment.

Please refer to FIG. 1C, the structure of the miniaturized particulate matter detector in FIG.1B is same as that in the first embodiment mentioned. The difference is each of two sides of the detect area 142 of the concentration detector 14 in FIG. 1C dispose an air hole 144, respectively. In one embodiment, the concentration detector 14 may be, but not limited to an integrated circuit (IC) chip.

In the above embodiments, a diameter of the plurality of holes is provided to allow an air flow passing through, and the air flow carries at least one particle of the particle millimeter 2.5 (PM 2.5); or to allow an air flow passing through, and the air flow containing at least one miniaturized particulate matter 146 to be detected. In one embodiment, the cross-sectional area having the larger area of the holes 16 is facing to the detect area 142, and this makes the air flow carrying the at least one miniaturized particulate matter 146 may pass through the cross-sectional area having the smaller area of the holes 16 (predetermined diameter of hole) and may be selected to enter the detect area 142 to disperse from the cross-sectional area having the larger area of the holes 16 to the detect area 142. Hence, the embodiments of the disclosure uses a semiconductor advanced process to make the TSV wafer serve as the filter 12 of the at least one miniaturized particulate matter 146, and acts with the designs of the diameter and the shape of the holes 16. This may reduce the blocking situations during selecting and filtering the at least one miniaturized particulate matter 146.

Figure 2A:
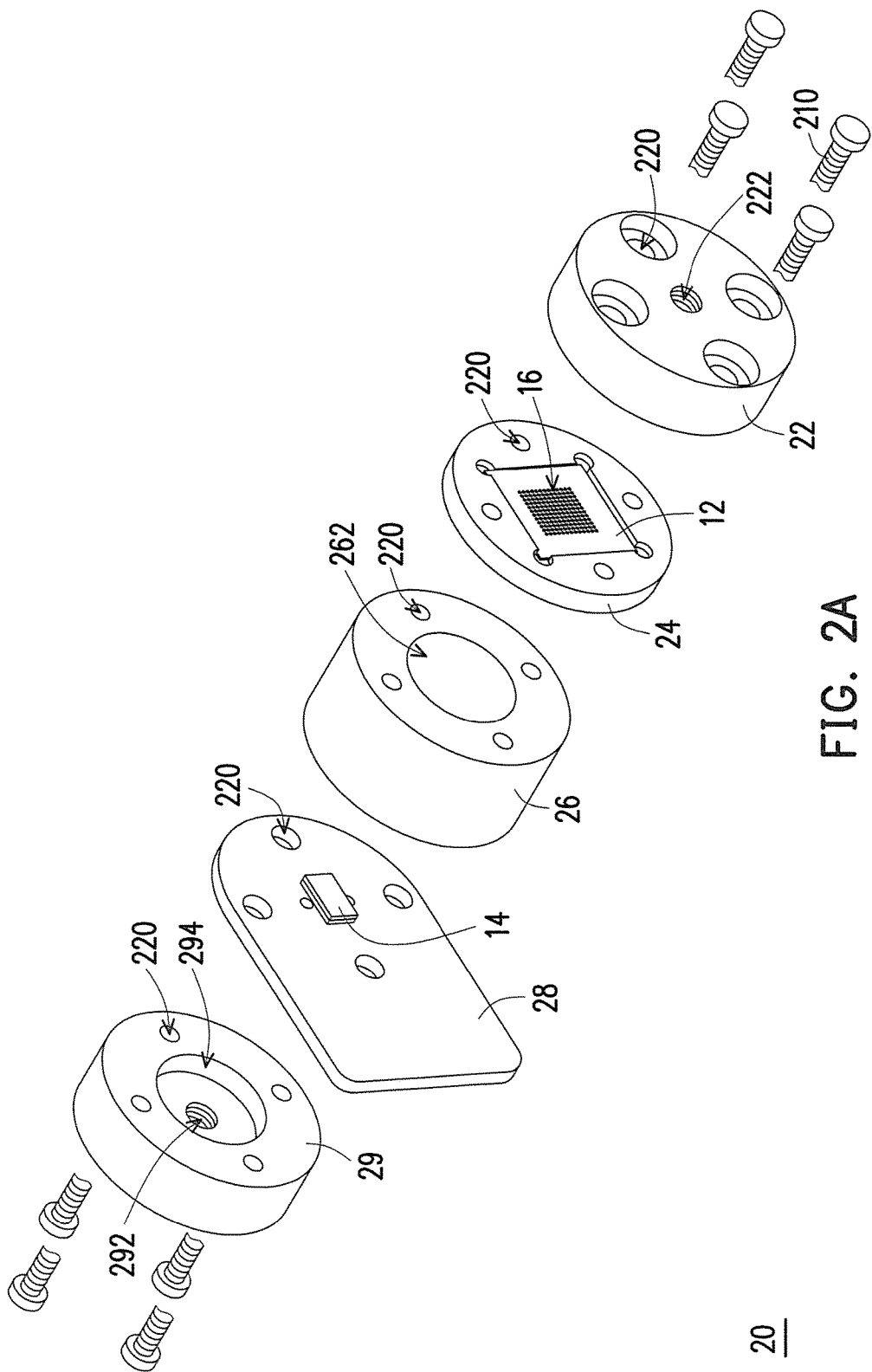
FIG. 2A is an exploded perspective schematic view of a miniaturized particulate matter detector according to an exemplary embodiment.

In an embodiment, the concentration detector 14 disposed on a printed circuit board (PCB) 28, as shown in FIG. 2A.

And, each of two sides of the concentration detector 14 both sides is disposed an air hole 144 respectively, as shown in FIG. 1C.

In an embodiment, an oscillator 141 and a circuit 143 are included in the detect area 142. The oscillator 141 is electrically connected to the circuit 143. When the at least one miniaturized particulate matter 146 is attached to the oscillator 141, the oscillation frequency of the oscillator 141 is transferred into the mass change and the concentration of the at least one miniaturized particulate matter 146 is detected.

Figure 1D:
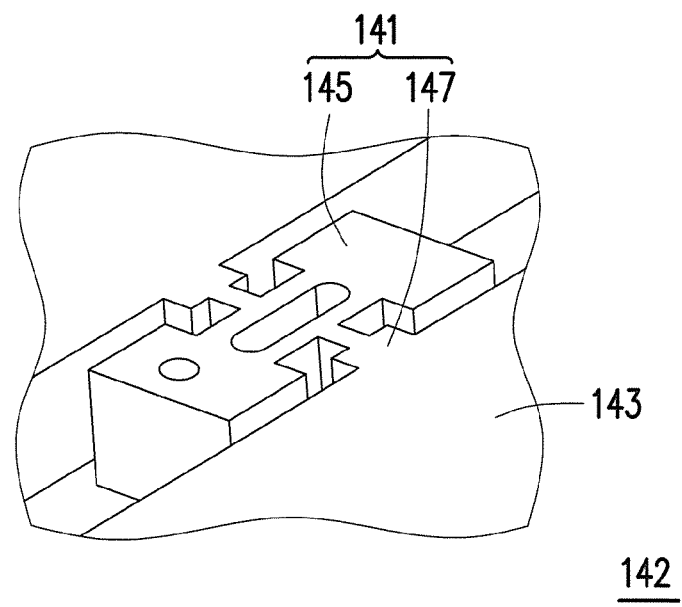
FIG. 1D is a schematic view of an oscillator according to an exemplary embodiment.

Please refer to FIG. 1D, the oscillator 141 further includes an oscillated element 145 and a spring 147 disposed at each of two sides of the oscillated element 145, respectively. The spring 147 is connected to the circuit 143. The circuit 143 is disposed on a circuit board 28, and the circuit 143 is electrically connected to the circuit board 28. In one embodiment, the circuit 143 located under the detect area 142. In an embodiment, the concentration detector 14 has at least one conductor 148 connected to the circuit board 28. The circuit 143 may be, but not limited to an IC chip. The oscillator 141 may be, but not limited to a Micro Electro-Mechanical System (MEMS) oscillator or a quartz oscillator.

Figure 1E:
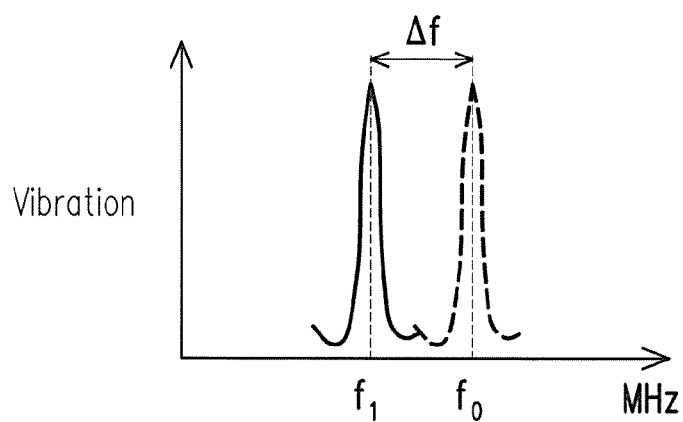
FIG. 1E and FIG. 1F are schematic views illustrating the working principle of an oscillator according to an exemplary embodiment.
Figure 1F:
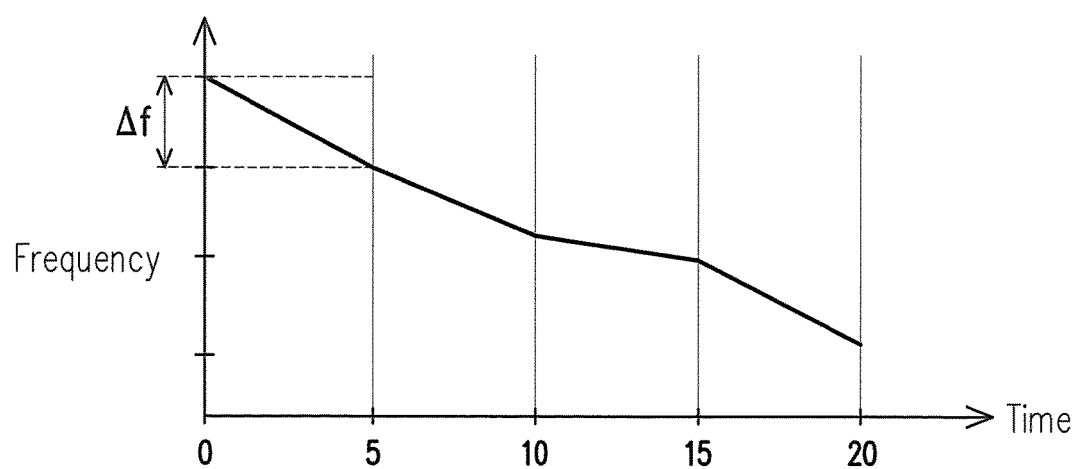

FIG. 1E and FIG. 1F are schematic views illustrating the working principle of an oscillator according to an exemplary embodiment. As shown in FIG. 1E, the vertical axis represents the number of oscillations, and the horizontal axis is represents the frequency. The formula is as follows:

$$f = \frac{1}{2\pi}\sqrt{\frac{k}{m}} \Rightarrow \frac{\Delta f}{f} = -\frac{\Delta m}{2m}.$$

As shown in FIG. 1F, the vertical axis represents the frequency, and the horizontal axis is represents the time. When the at least one miniaturized particulate matter 146 is attached to the oscillator 141, the oscillation frequency decreases, therefore, the oscillation frequency is transferred into the mass change and the concentration of the at least one miniaturized particulate matter 146 is detected.

FIG. 2A is an exploded perspective schematic view of a miniaturized particulate matter detector according to an exemplary embodiment. As shown in the embodiment of FIG. 2A, the miniaturized particulate matter detector 10 further includes an intermediate element 26, a top cover 22 and a bottom cover 29. The intermediate element 26 has a first through-holes 262 and the intermediate element 26 is disposed between the filter 12 and the concentration detector 14. The intermediate element 26 is disposed between a support plate 24 and the circuit board 28. The first through-hole 262 aligns with the plurality of holes 16 and the concentration detector 14 to make the air flow easily pass through the first through-hole 262. The intermediate element 26, the top cover 22 and the bottom cover 29 may have the same geometric shape. In one embodiment, the intermediate element 26, the top cover 22 and the bottom cover 29 may have a round shape to easily assembly a module or dismount the module.

Figure 6:
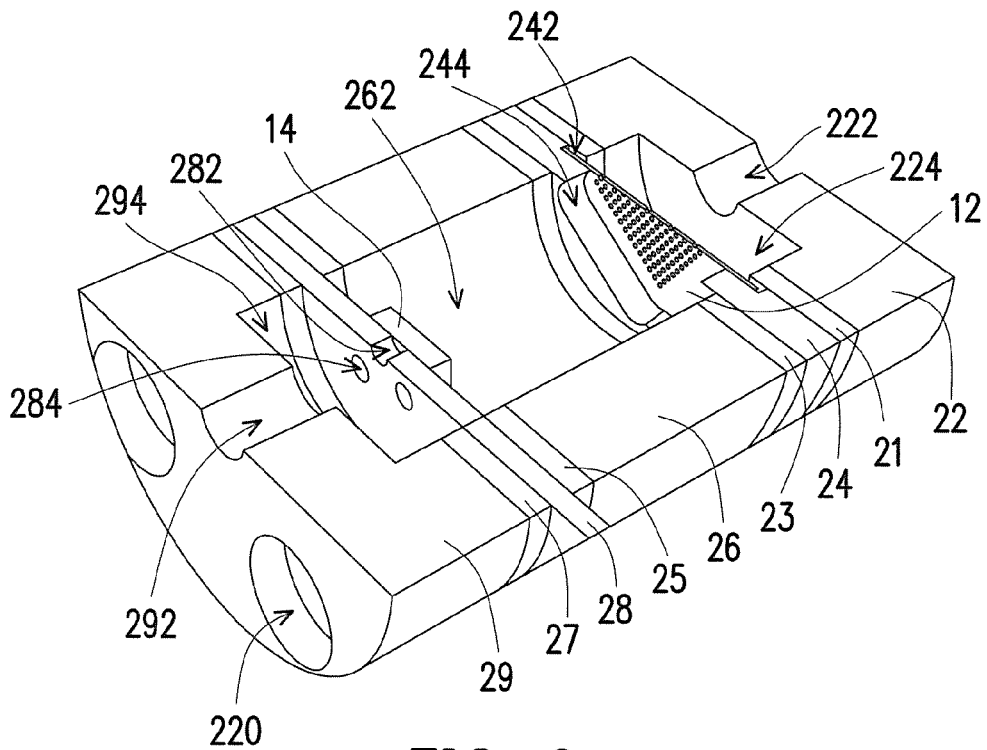
FIG. 6 is an assembled cross-sectional schematic view of a miniaturized particulate matter detector according to a tenth exemplary embodiment.

The filter 12 is disposed between the top cover 22 and the intermediate element 26. The top cover 22 has an air inlet 222. The circuit board 28 is disposed between the bottom cover 29 and the intermediate element 26. The bottom cover 29 has an air outlet 292. In an embodiment, an inside surface of the top cover 22 has a first recess 224 (as shown in FIG. 6), and an inside surface of the bottom cover 29 has a second recess 294. The first recess 224 and the second recess 294 communicate with the air inlet 222 and the outlet 292 respectively.

Figure 2B:
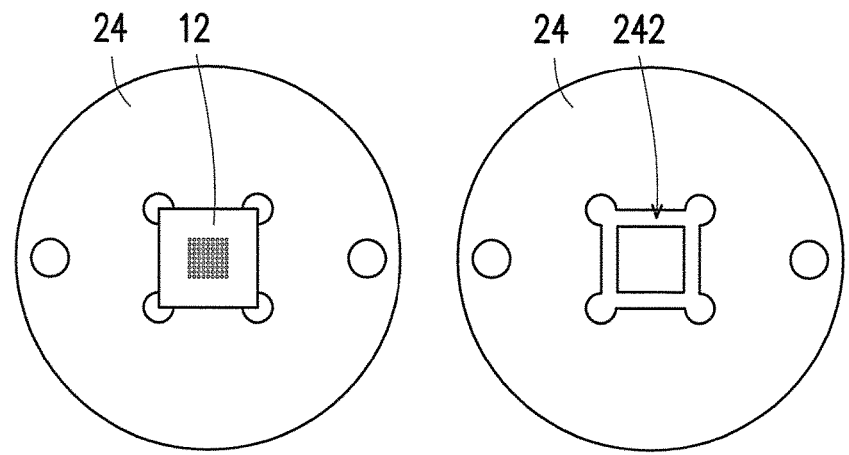
FIG. 2B is a perspective schematic view of a filter according to an exemplary embodiment.

FIG. 2B is an exploded perspective schematic view of a filter according to an exemplary embodiment. As provided in the embodiment that is depicted in FIG. 2B, the filter 12 is disposed on the support plate 24 having a recess 242 thereon. The filter 12 is inserted into and fixed inside the recess 242. The support plate 24 has a fifth through-hole 244 (and shown in FIG. 6) that links the filter 12.

As shown in FIG. 2A and FIG. 2B, the top cover 22, the support plate 24, the intermediate element 26, the circuit board 28 and the bottom cover 29 dispose, respectively, a plurality of lock holes 220 thereon, to provide a plurality of keys 210 to lock the plurality of lock holes 220, and to fix the top cover 22, the support plate 24, the intermediate element 26, the circuit board 28 and the bottom cover 29 as one module 20.

Figure 3:
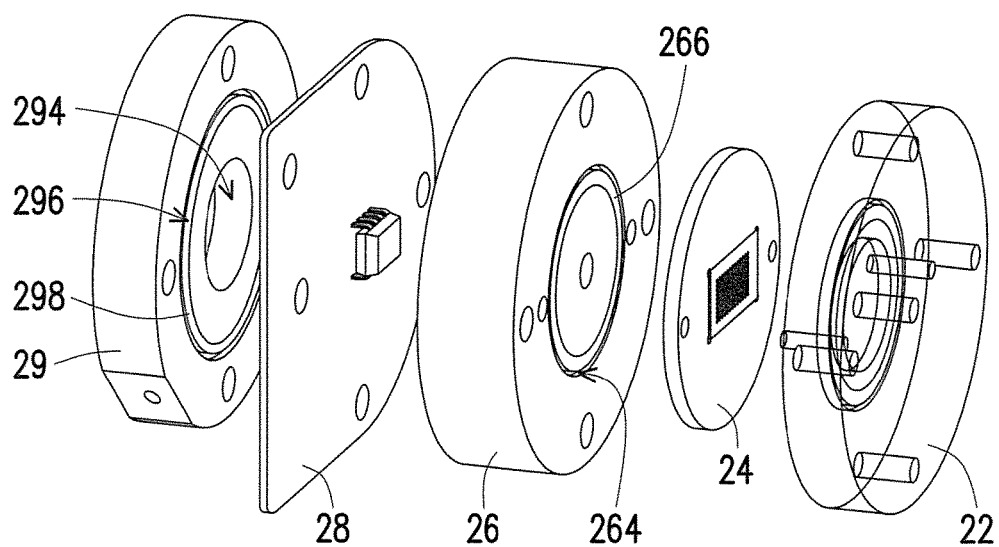
FIG. 3 is an exploded perspective schematic view of a miniaturized particulate matter detector according to a fourth exemplary embodiment.

FIG. 3 is an exploded perspective schematic view of a miniaturized particulate matter detector according to a fourth exemplary embodiment. As shown in the embodiment of FIG. 3, each of the two sides of the intermediate element 26 has a first groove 264 around the first through-hole 262 to provide a first seal element 266 embedded inside the first groove 264. A first Inside surface of the top cover 22 and a second inside surface of the bottom cover 29 have a second groove and a third groove (not shown in the drawings), respectively, to provide a second seal element (not shown in the drawings) and a third seal element 298, and the second seal element and the third seal element 298 are embedded in the second groove and the third groove 296 respectively. The first seal element 266 and the third seal element 298 provide a seal effect, therefore, the air flow passes through the filter 12 and the detector 14 without occurring any leakage. The embodiments of the disclosure may use a fixture design to change the filter 12 or the concentration detector 14 to repeatedly use the miniaturized particulate matter detector 10.

Figure 4:
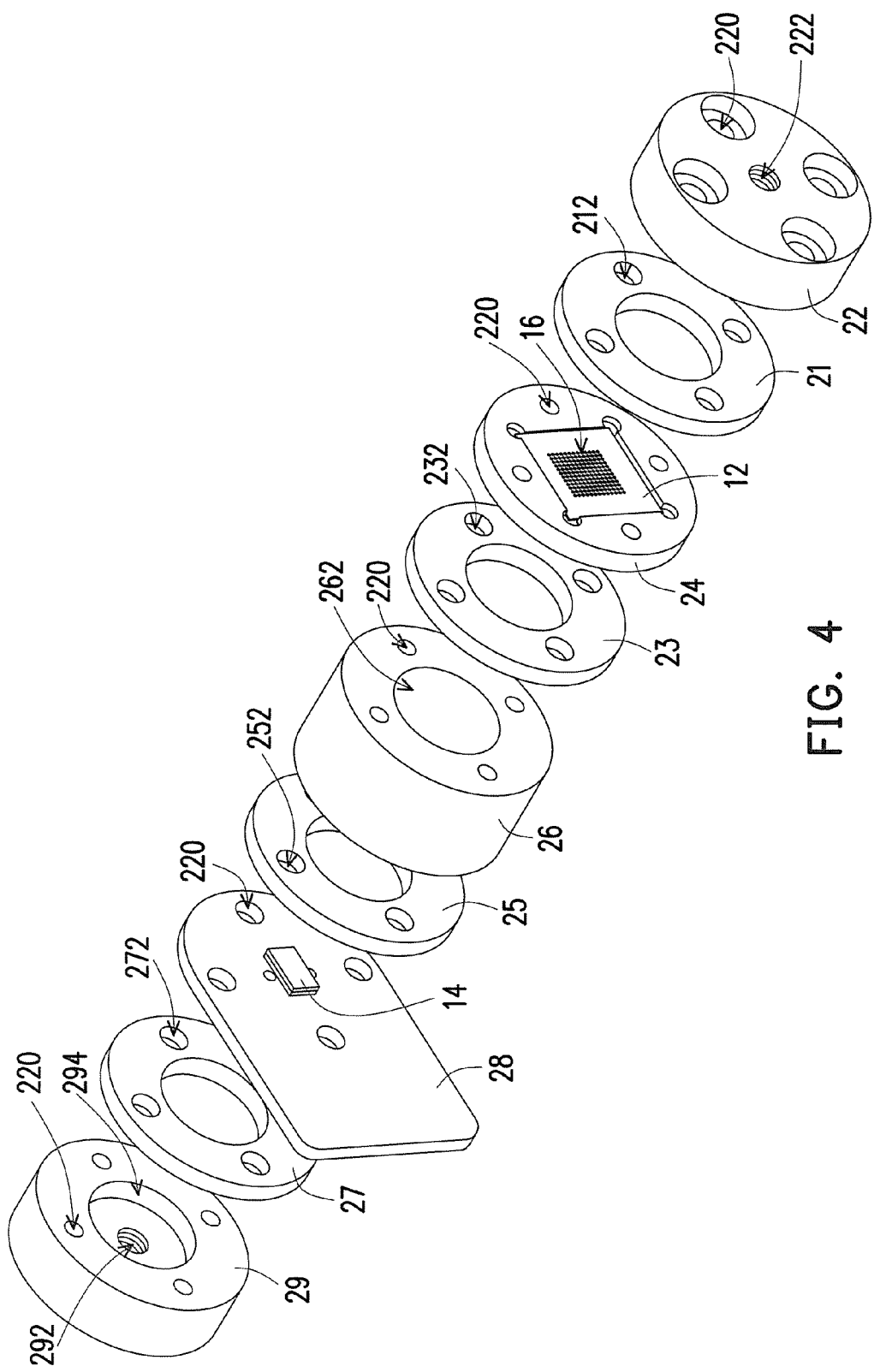
FIG. 4 is an exploded perspective schematic view of a miniaturized particulate matter detector according to a fifth exemplary embodiment.

FIG. 4 is an exploded perspective schematic view of a miniaturized particulate matter detector according to a fifth exemplary embodiment. As shown in the embodiment of FIG. 4, gaskets 21, 23, 25, and 27 are disposed between the top cover 22 and the support plate 24, between the support plate 24 and the intermediate element 26, between the intermediate element 26 and the circuit board 28, and between the circuit board 28 and the bottom cover 29, respectively, to provide a sealing effect and a buffering effect. The four gaskets 21, 23, 25, and 27 respectively have their own multiple locks 212, 232, 252, and 272 corresponding to the top cover 22, the support plate 24, the intermediate element 26, the circuit board 28, and the lock holes 220 of the bottom cover 29, as shown in FIG. 4.

Figure 5A:
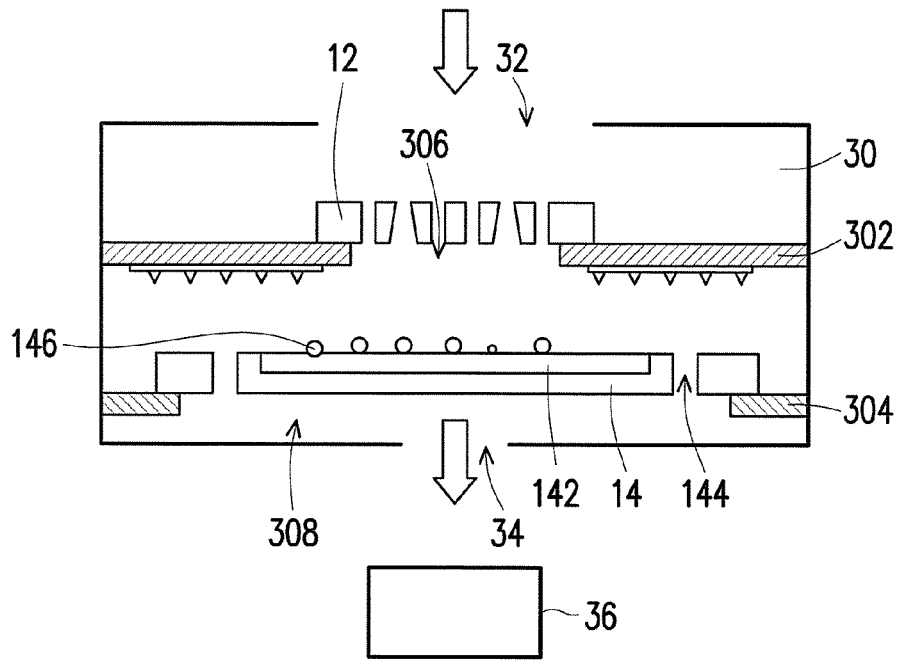
FIG. 5A is a cross-sectional schematic view of a miniaturized particulate matter detector according to a sixth exemplary embodiment.

FIG. 5A is a cross-sectional schematic view of a miniaturized particulate matter detector according to a sixth exemplary embodiment. As shown in the embodiment of FIG. 5A, a fixture 30 includes an inlet 32 and an outlet 34. A first support plate 302 and a second support plate 304 are disposed in the fixture 30. The first support plate 302 locates above the second support plate 304. The first support plate 302 has a third through-hole 306, and the filter 12 is disposed on the third through-hole 306. The second support plate 304 has a fourth through-hole 308, and the concentration detector 14 is disposed on the fourth through-hole 308. The concentration detector 14 has one or more air holes 144.

In an embodiment, a pump 36 is disposed at an outlet 34 of the fixture 30. The air flow may enter the filter 12 via an inlet 32 of the fixture 30, to filter the at least one miniaturized particulate matter 146. The at least one miniaturized particulate matter 146 that may pass through the filter 12 is attached to the detect area 142 of the concentration detector 14, therefore, the concentration of the at least one miniaturized particulate matter 146 is obtained.

In an embodiment, the interior of the fixture 30 may be cut into three spaces through the first support plate 302 and the second support plate 304. Thus, the air flow may be driven by the pump 36, and passes through the filter 12, the concentration detector 14, the air holes 144 from the inlet 32 of the fixture 30, then flows out form the outlet 34 of the fixture 30.

In an embodiment, after the filter 12 and the concentration detector 14 are modularized, the modularized filter 12 and the modularized concentration detector 14 may be disassembled and replaced.

Figure 5B:
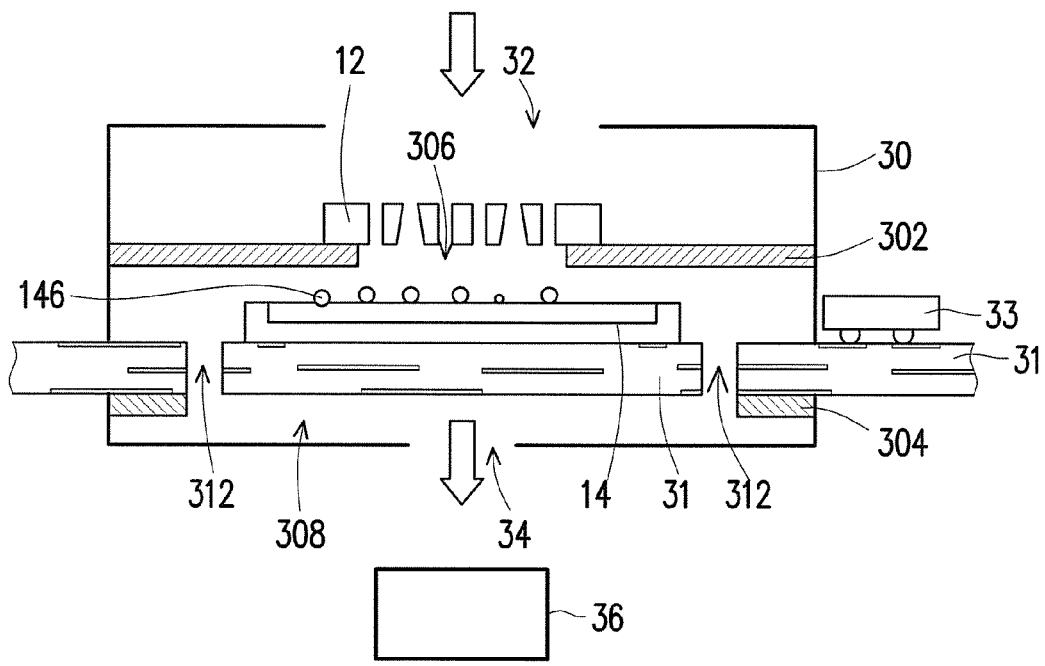
FIG. 5B is a cross-sectional schematic view of a miniaturized particulate matter detector according to a seventh exemplary embodiment.

FIG. 5B is a cross-sectional schematic view of a miniaturized particulate matter detector according to a seventh exemplary embodiment. Basically, the embodiment in FIG. 5B is similar to that in FIG. 5A. As shown in the embodiment of FIG. 5B, the difference is a printer circuit board 31 (PCB) is disposed on the second support plate 304, and the PCB 31 is protruding from the fixture 30 to connect to another chip 33 or substrate and so on. The concentration detector 14 is electrically connected to and disposed on the PCB 31. In one embodiment, the concentration detector 14 has one or more air through holes (not shown in drawings). The pump 36 is disposed at the outlet 34 of the fixture 30 to drive the air flow. In one embodiment, the PCB 31 has a plurality of air through holes (not shown in drawings). Thus, the air flow may enter the filter 12 via the inlet 32 of the fixture 30, to filter the at least one miniaturized particulate matter 146. The at least one miniaturized particulate matter 146 that may pass through the filter 12 is attached to the detect area 142 of the concentration detector 14 the concentration of the at least one miniaturized particulate matter 146 is obtained. Then, the air flow may flow out form the outlet 34 of the fixture 30 via air through-holes 312.

Figure 5C:
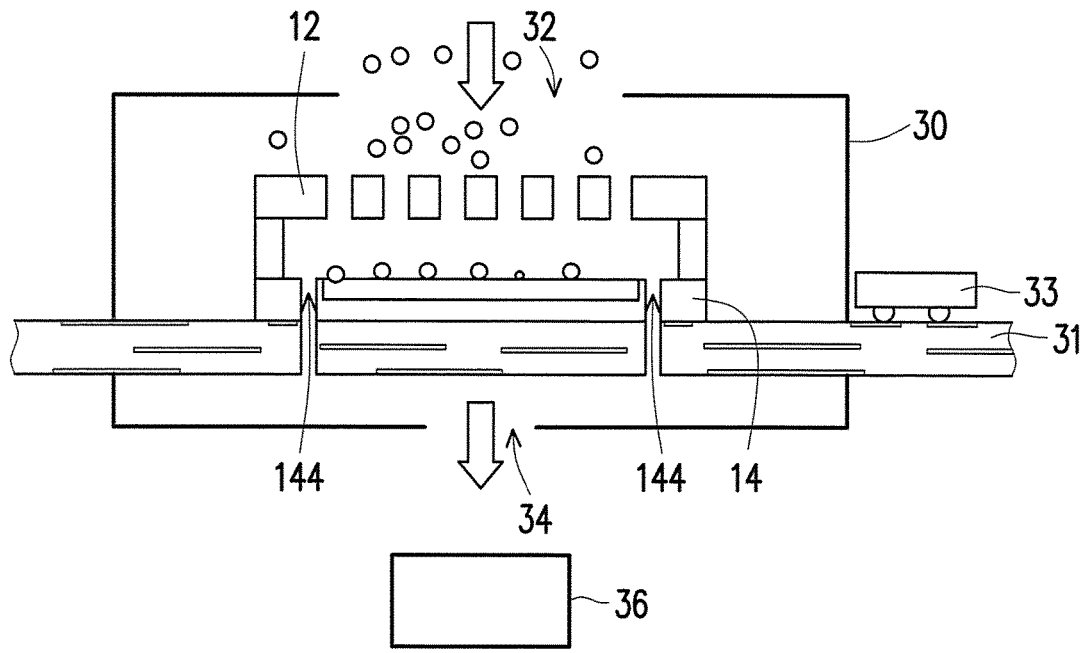
FIG. 5C is a cross-sectional schematic view of a miniaturized particulate matter detector according to an eighth exemplary embodiment.

FIG. 5C is a cross-sectional schematic view of a miniaturized particulate matter detector according to an eighth exemplary embodiment. In the embodiment of FIG. 5C, the embodiment shown in FIG. 1C is disposed on the PCB 31, and the air through-hole 144 of the concentration detector 14 passes through the PCB 31. Herein, the air flow may enter the filter 12 and the concentration detector 14 via the inlet 32 of the fixture 30, the air flow then passes through the air through-holes 144 and flows out from the outlet 34 of the fixture 30. The pump 36 is disposed at the outlet 34 of the fixture 30 to drive the air flow.

Figure 5D:
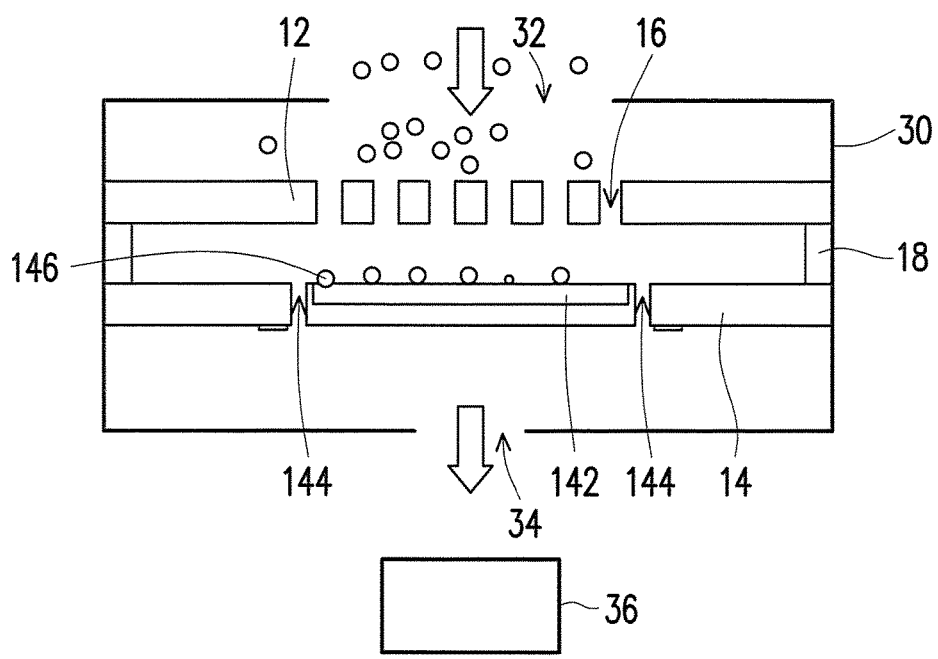
FIG. 5D is a cross-sectional schematic view of a miniaturized particulate matter detector according to a ninth exemplary embodiment.

FIG. 5D is a cross-sectional schematic view of a miniaturized particulate matter detector according to a ninth exemplary embodiment. In the embodiment of FIG. 5D, the embodiment shown in FIG. 1C is disposed on an inside surface of the fixture 30. The air flow may enter the filter 12, the concentration detector 14, and the air through holes 144 via the inlet 32 of the fixture 30, the air flow then flows out from the outlet 34 of the fixture 30. The pump 36 is disposed at the outlet 34 of the fixture 30 to drive the air flow. Same as shown in FIG. 1C, an adhesive material 18 is disposed between the filter 12 and the concentration detector 14 of FIG. 5D to bonding the filter 12 and the detector 14.

Figure 5E:
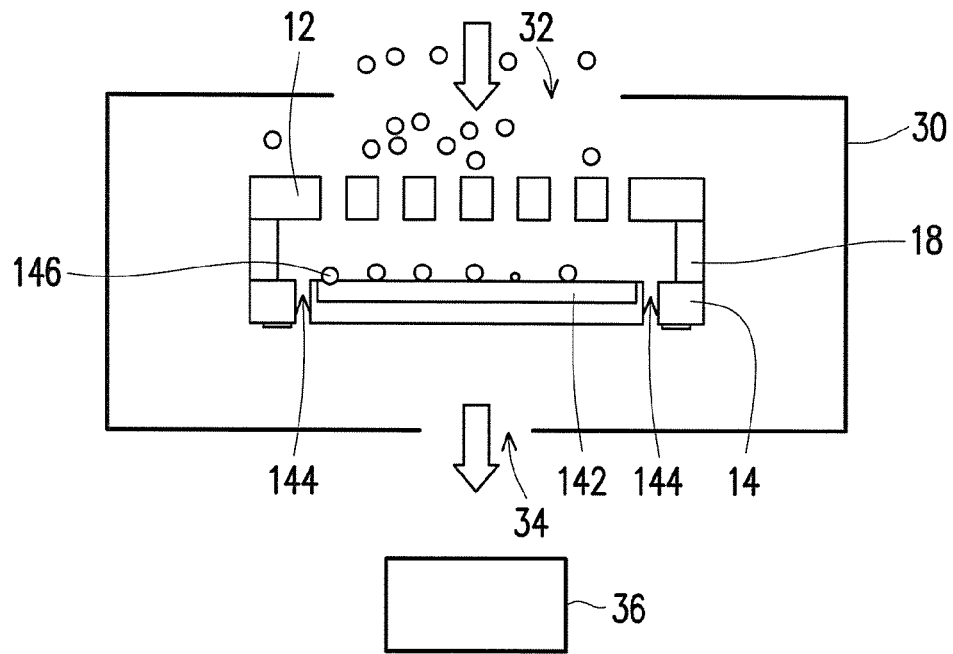
FIG. 5E is a ross-sectional schematic view of a miniaturized particulate matter detector according to a tenth exemplary embodiment.

FIG. 5E is cross-sectional schematic view of a miniaturized particulate matter detector according to a tenth exemplary embodiment. In the embodiment of FIG. 5E, the embodiment shown in FIG. 1C is disposed on the interior of the fixture 30. The air flow may enter the filter 12, the interior of the fixture 30, and the concentration detector 14 via the inlet 32 of the fixture 30, the air flow then flows out from the outlet 34 of the fixture 30. In one embodiment, the concentration detector 14 does not have the air through-hole. In one embodiment, the pump 36 is disposed at the outlet 34 of the fixture 30 to drive the air flow.

FIG. 6 is an assembled cross-sectional schematic view of a miniaturized particulate matter detector according to a tenth exemplary embodiment. Please refer to FIG. 6, after modularization, a gasket 21 is disposed between the top cover 22 and the support plate 24. The top cover 22 has an air inlet 222, and there is a first recess 224 inside the top cover 22 to communicate with the air inlet 222. The filter 12 is disposed on the support plate 24 to correspond to the fifth through-hole 244 of the support plate 24, and then the air flow passes through the filter 12 and the fifth through-hole 244. The gasket 25 is disposed between the intermediate element 26 and the circuit board 28. The concentration detector 14 is disposed on the circuit board 28, and the circuit board 28 has a second through-hole 282 corresponding to the oscillator 141 of the concentration detector 14. The second through-hole 282 is disposed on the circuit board 28 to correspond to the concentration detector 14, and this may make the air flow pass through the oscillator 141 of the concentration detector 14, then enter the second through-hole 282. On the circuit board 28, at least one first air through-hole 284 may be disposed at both sides of the concentration detector 14. The first through-hole 262 of the intermediate element 26 may communicate with the fifth through-hole 244 of the support plate 24, the first air through-hole 284 and the second air through-hole 282, respectively. There is a second recess 294 in the inside of the bottom cover 29, which communicates with the air outlet 292, the first air through hole 284 and the second through hole 282, respectively. A gasket 27 is disposed between the bottom cover 29 and the circuit board 28. A gasket 25 is disposed between the intermediate element 26 and the circuit board 28. The top cover 22, the support plate 24, the intermediate element 26, the circuit board 28 and the bottom cover 29 may use a plurality of keys to lock the plurality of lock holes. After these components in the aforementioned embodiments of the disclosure are modularized, the modularized products of the disclosure may be miniaturized, easy to carry, real-time proceeding to detect the at least one miniaturized particulate matter 146.

Figure 7:
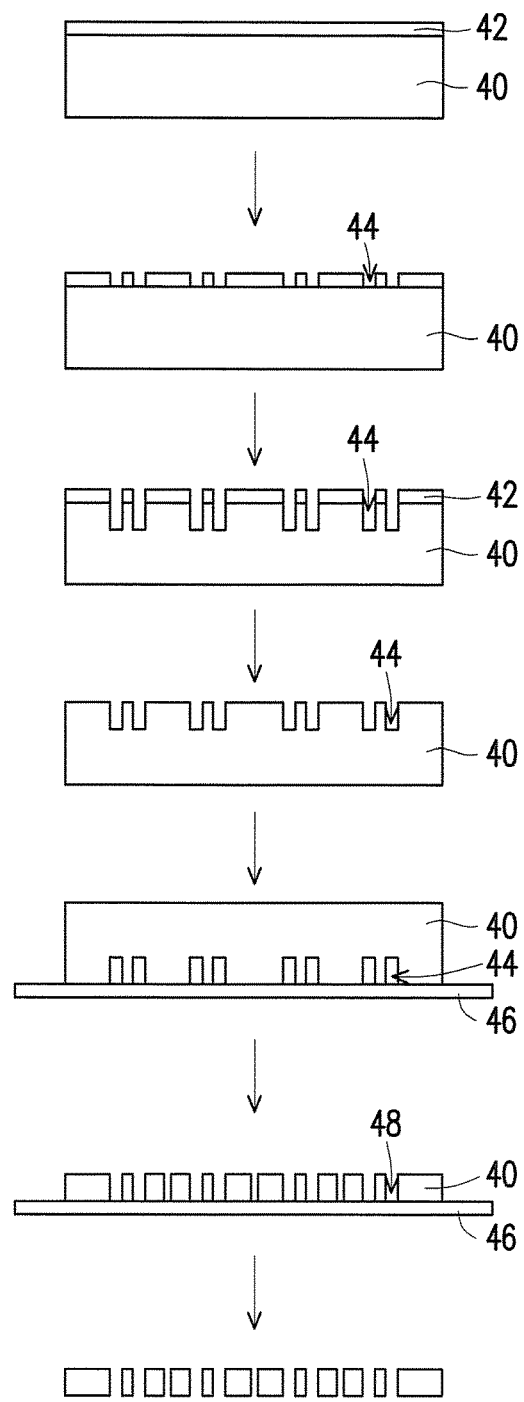
FIG. 7 is a schematic view of a manufacturing method of a filter according to an exemplary embodiment.

FIG. 7 is a schematic view of a manufacturing method of a filter according to an exemplary embodiment. Please refer to FIG. 7, the manufacture method of the filter may comprise: providing a substrate 40; coating or lithographic printing a photoresist material 42 on the substrate 40; etching a plurality of openings 44 on the substrate 40, wherein the plurality of openings 44 have an opening shape of gradually reducing, or gradually expanding or cylindrical; removing the photoresist material 42 from the substrate 40; pasting a first support plate 46 on a surface of the plurality of openings 44 of the substrate 40; grinding the substrate 40 until to expose the plurality of openings 44 to form a plurality of through-silicon vias (TSVs) 48; and cutting the substrate 40 and includes a plurality of TSV 48.

Figure 8A:
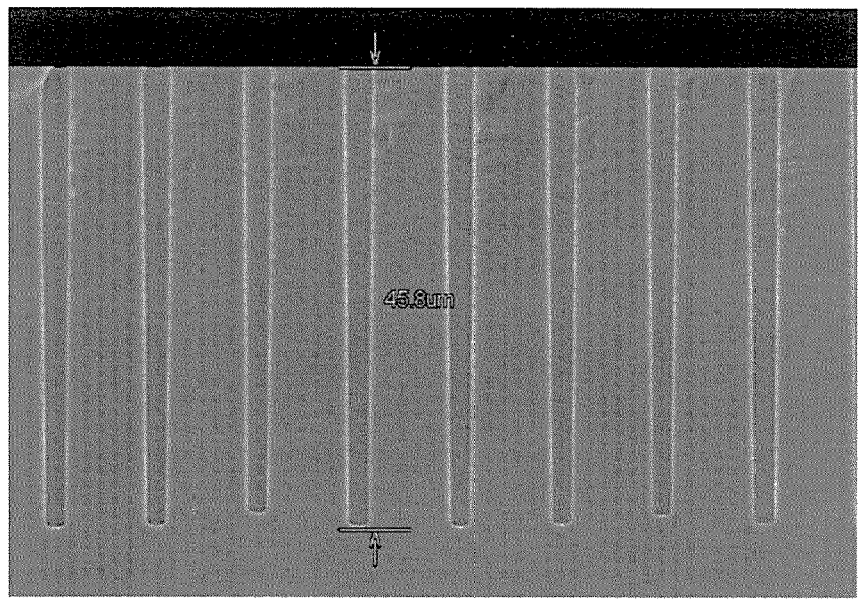
FIG. 8A, FIG. 8B, and FIG. 8C are schematic views of TSV images of a filter according to an exemplary embodiment.
Figure 8B:
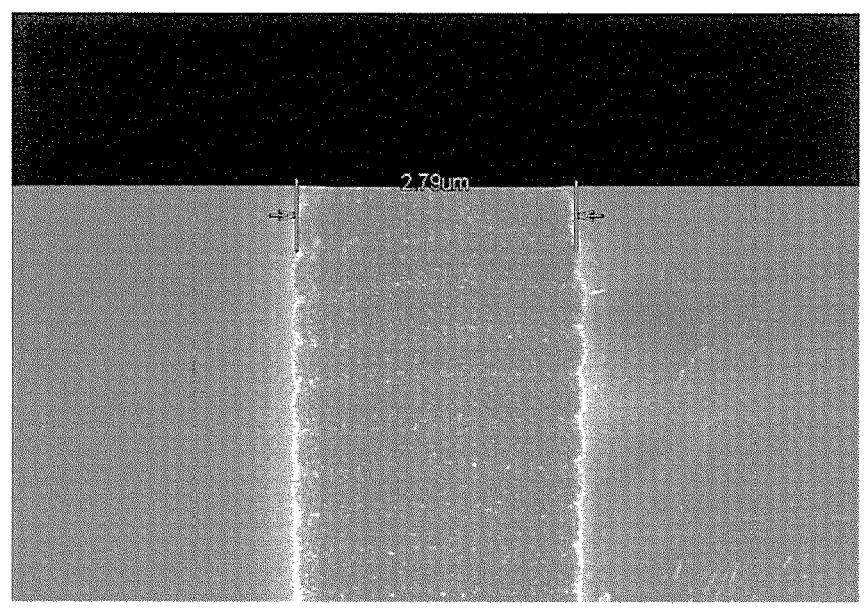
Figure 8C:
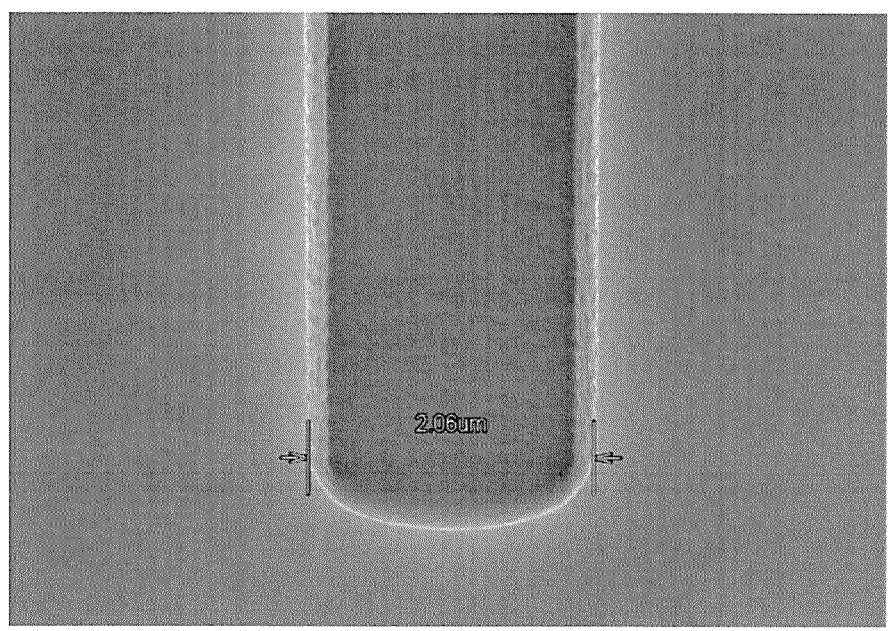

FIG. 8A, FIG. 8B, and FIG. 8C are schematic views of TSV images of a filter according to an exemplary embodiment. Please refer to FIG. 8A, FIG. 8B, and FIG. 8C, the opening size may be obtained by using the developer and an etching scheme, and use using the etching scheme may etch specific angles for the holes, as shown in FIG. 8A. In FIG. 8A, the TVS is made by using etching, and the etching depth is 45 um. It may be seen from FIG. 8B and FIG. 8C, the central diameter (CD) of the top is 2.79 μm and the CD of the bottom is 2.06 μm. The filter may be obtained by grinding, polishing and cutting the wafer.

Figure 9A:
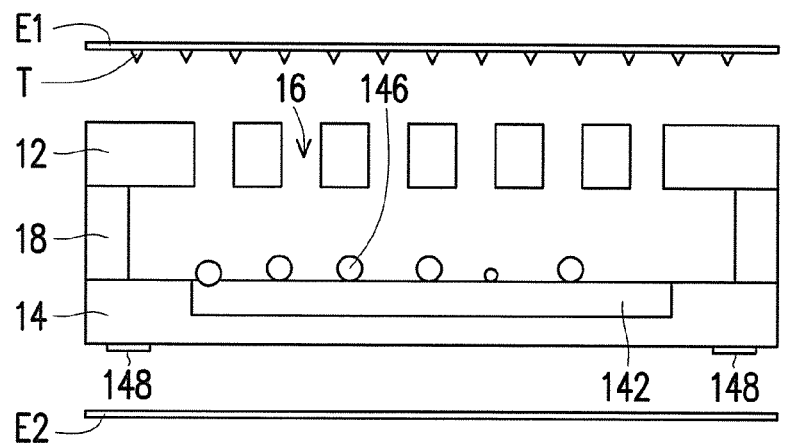
FIG. 9A to FIG. 9C are cross-sectional schematic views of a miniaturized particulate matter detector according to an eleventh exemplary embodiment.
Figure 9B:
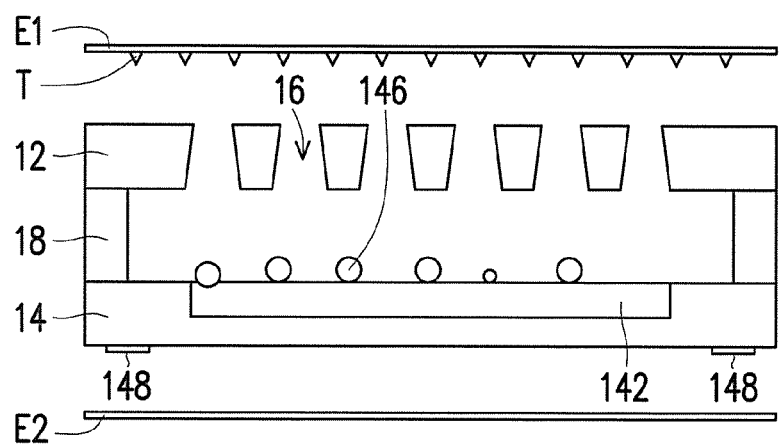
Figure 9C:
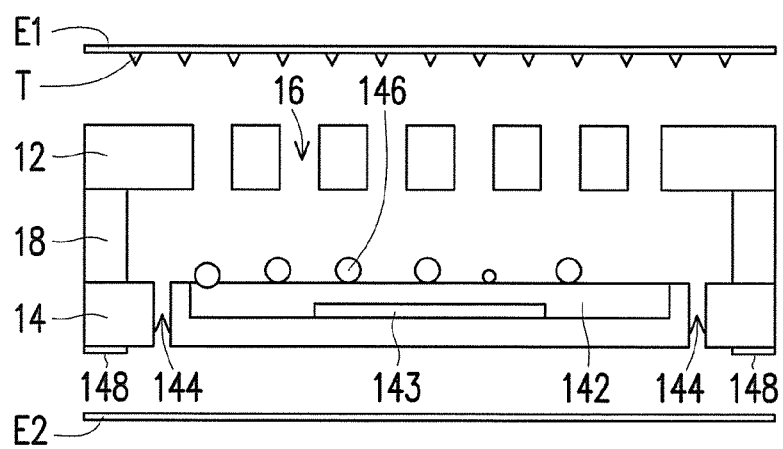

FIG. 9A to FIG. 9C are cross-sectional schematic views of a miniaturized particulate matter detector according to an eleventh exemplary embodiment. With reference to FIG. 1A to FIG. 1C and FIG. 9A to FIG. 9C, the miniaturized particulate matter detector shown in FIG. 9A to FIG. 9C and provided in the present embodiment is similar to the miniaturized particulate matter detectors provided in the first embodiment to the third embodiment (FIG. 1A to FIG. 1C), while the differences therebetween are provided below. In the present embodiment, the miniaturized particulate matter detector further includes a first electrode E1 and a second electrode E2. The first electrode E1 has a plurality of discharge tips T pointing at the concentration detector 14, and the discharge tips T are suitable for charging the miniaturized particulate matter 146. Besides, the concentration detector 14 is located between the first electrode E1 and the second electrode E2, and the first electrode E1 and the second electrode E2 are adapted to generate an electric field at least applied between the filter 12 and the concentration detector 14, so as to drive the charged miniaturized particulate matter 146 toward the concentration detector 14 from the filter 12, and the charged miniaturized particulate matter 146 is attached to the detect area 142 of the concentration detector 14.

As shown in FIG. 9A to FIG. 9C, in the present embodiment, the filter 12 and the concentration detector 14 are located between the first electrode E1 and the second electrode E2, such that the electric field between the first electrode E1 and the second electrode E2 can be applied between the filter 12 and the concentration detector 14. In the present embodiment, the first electrode E1 is electrically connected to a negative voltage and located above the filter 12, for instance, and the second electrode E2 is electrically connected to a positive voltage and located below the concentration detector 14, for instance. The discharge tips T of the first electrode E1 are, for instance, conductive bumps with tips, for instance, and the discharge tips T (i.e., the conductive bumps) are stud bumps formed by performing a wire-bonding process, for instance. Besides, the discharge tips T may also be gold bumps or conductive bumps made of other materials, for instance.

However, the locations of the first and second electrodes E1 and E2 are not limited to those depicted in FIG. 9A to FIG. 9C, i.e., in principle the electric field between the first electrode E1 and the second electrode E2 is required to be applied between the filter 12 and the concentration detector 14. Another way to arrange the first electrode E1 and the second electrode E2 is described hereinafter with reference to FIG. 10A to FIG. 10C.

Figure 10A:
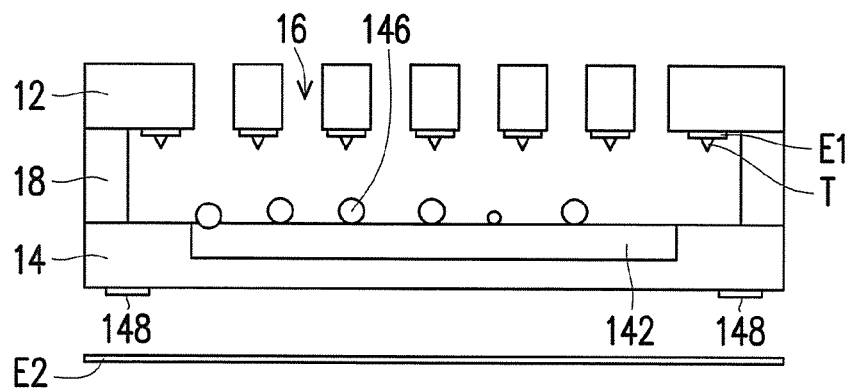
FIG. 10A to FIG. 10C are cross-sectional schematic views of a miniaturized particulate matter detector according to a twelfth exemplary embodiment.
Figure 10B:
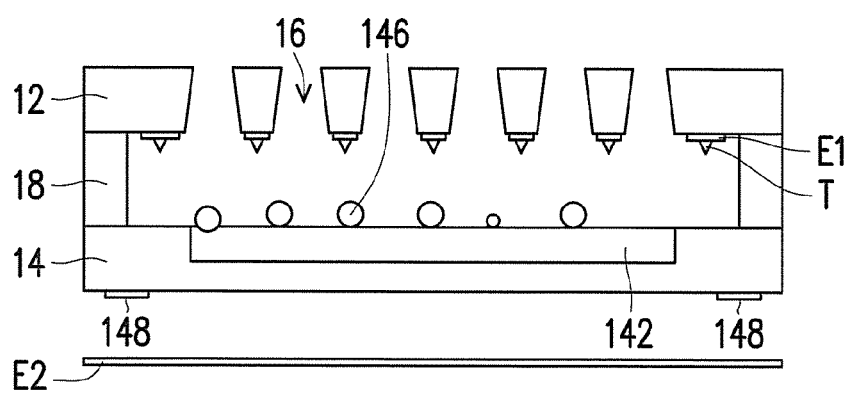
Figure 10C:
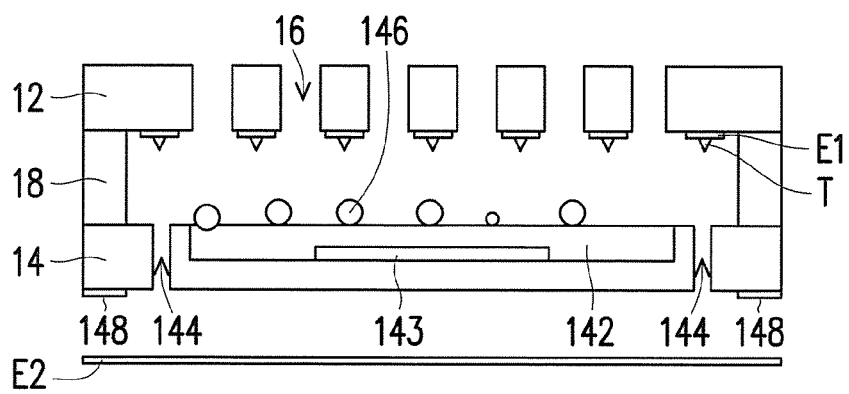

FIG. 10A to FIG. 10C are cross-sectional schematic views of a miniaturized particulate matter detector according to a twelfth exemplary embodiment. With reference to FIG. 9A to FIG. 9C and FIG. 10A to FIG. 10C, the miniaturized particulate matter detector shown in FIG. 10A to FIG. 10C and provided in the present embodiment is similar to the miniaturized particulate matter detector provided in the eleventh embodiment (FIG. 9A to FIG. 9C), while the difference therebetween lies in that the first electrode E1 is located on the lower surface of the filter 12 according to the present embodiment. That is, the first electrode E1 is located between the filter 12 and the concentration detector 14, and the electric field between the first electrode E1 and the second electrode E2 is applied to the first electrode E1 and the concentration detector 14 but does not affect the miniaturized particulate matter 146 above the filter 12.

In the miniaturized particulate matter detector shown in FIG. 10A to FIG. 10C, the manufacturing process of the first electrode E1 can be integrated into the manufacturing process of the filter 12, and therefore the volume of the miniaturized particulate matter detector can be further reduced.

As provided above, the first electrode E1 and the second electrode E2 described in the eleventh embodiment and the twelfth embodiment are also applicable in the sixth embodiment to the tenth embodiments (shown in FIG. 5A to FIG. 5E), and different ways to arrange the first and second electrodes E1 and E2 are described hereinafter with reference to FIG. 11A to FIG. 11E.

Figure 11A:
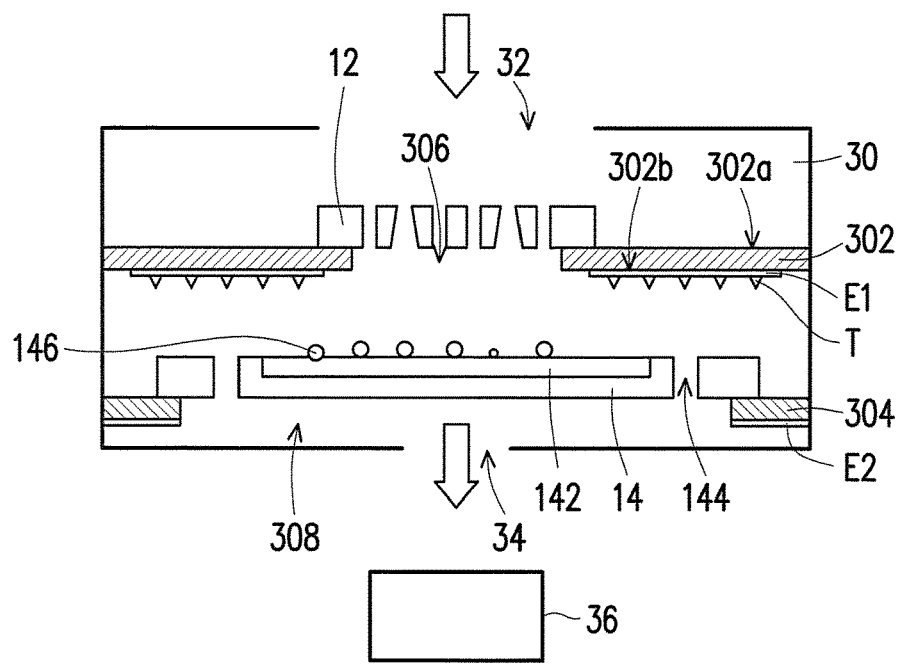
FIG. 11A is a cross-sectional schematic view of a miniaturized particulate matter detector according to a thirteenth exemplary embodiment.

FIG. 11A is a cross-sectional schematic view of a miniaturized particulate matter detector according to a thirteenth exemplary embodiment. With reference to FIG. 5A and FIG. 11A, the miniaturized particulate matter detector shown in FIG. 11A and provided in the present embodiment is similar to the miniaturized particulate matter detector provided in the sixth embodiment (FIG. 5A), while the difference therebetween lies in that the miniaturized particulate matter detector provided in the present embodiment further includes a first electrode E1 and a second electrode E2. The first electrode E1 has a plurality of discharge tips T pointing at the concentration detector 14, and the discharge tips T are suitable for charging the miniaturized particulate matter 146. Besides, as shown in FIG. 11A, in the present embodiment, the first support plate 302 has an upper surface 302a and a lower surface 302b, the filter 12 is located on the upper surface 302a of the first support plate 302, and the first electrode E1 is located on the lower surface 302b of the first support plate 302. The second support plate 304 is suitable for supporting the concentration detector 14, and the second electrode E2 is located on any surface (either the upper surface or the lower surface) of the second support plate 304.

In the present embodiment, the location of the first electrode E1 is not limited to be on the lower surface 302b of the first support plate 302, and the location of the second electrode E2 is not limited to be on the lower surface of the second support plate 304. For instance, the first electrode E1 may be located above the filter 12, and the second electrode E2 may be located on the bottom surface of the concentration detector 14 or on the fixture 30 below the concentration detector 14.

Figure 11B:
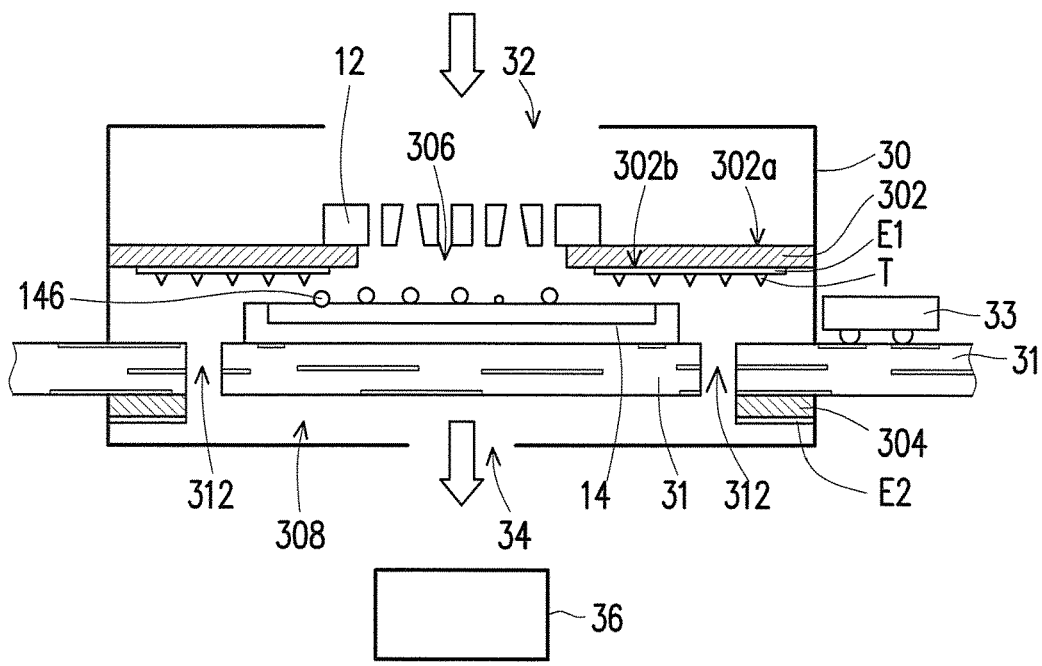
FIG. 11B is a cross-sectional schematic view of a miniaturized particulate matter detector according to a fourteenth exemplary embodiment.

FIG. 11B is a cross-sectional schematic view of a miniaturized particulate matter detector according to a fourteenth exemplary embodiment. With reference to FIG. 5B and FIG. 11B, the miniaturized particulate matter detector shown in FIG. 11B and provided in the present embodiment is similar to the miniaturized particulate matter detector provided in the seventh embodiment (FIG. 5B), while the difference therebetween lies in that the miniaturized particulate matter detector provided in the present embodiment further includes a first electrode E1 and a second electrode E2. The first electrode E1 has a plurality of discharge tips T pointing at the concentration detector 14, and the discharge tips T are suitable for charging the miniaturized particulate matter 146. Besides, as shown in FIG. 11B, in the present embodiment, the first support plate 302 has an upper surface 302a and a lower surface 302b, the filter 12 is located on the upper surface 302a of the first support plate 302, and the first electrode El is located on the lower surface 302b of the first support plate 302. The second support plate 304 is suitable for supporting the concentration detector 14 and the PCB 31, and the second electrode E2 is located on any surface (either the upper surface or the lower surface) of the second support plate 304.

In the present embodiment, the location of the first electrode E1 is not limited to be on the lower surface 302b of the first support plate 302, and the location of the second electrode E2 is not limited to be on the lower surface of the second support plate 304. For instance, the first electrode E1 may be located above the filter 12, and the second electrode E2 may be located between the PCB 31 and the concentration device 14, on the bottom surface of the PCB 31, or on the fixture 30 below the PCB 31.

Figure 11C:
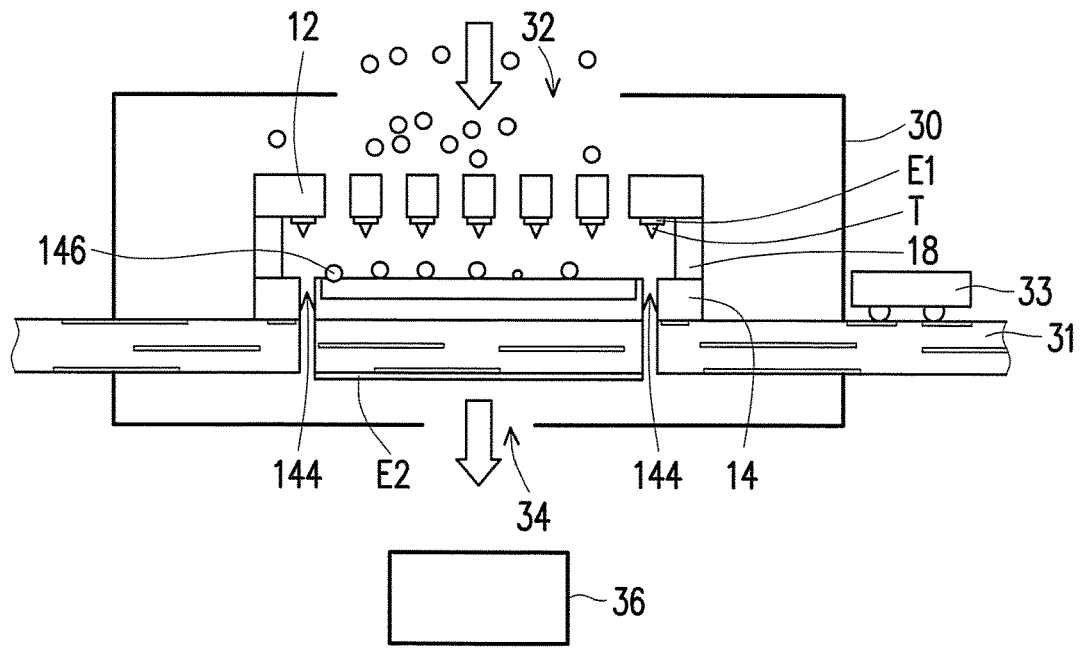
FIG. 11C is a cross-sectional schematic view of a miniaturized particulate matter detector according to a fifteenth exemplary embodiment.

FIG. 11C is a cross-sectional schematic view of a miniaturized particulate matter detector according to a fifteenth exemplary embodiment. With reference to FIG. 5C and FIG. 11C, the miniaturized particulate matter detector provided in the present embodiment is similar to the miniaturized particulate matter detector provided in the eighth embodiment, while the difference therebetween lies in that the miniaturized particulate matter detector provided in the present embodiment further includes a first electrode E1 and a second electrode E2. The first electrode E1 has a plurality of discharge tips T pointing at the concentration detector 14, and the discharge tips T are suitable for charging the miniaturized particulate matter 146. Besides, as shown in FIG. 11C, in the present embodiment, the first electrode E1 is located on the lower surface of the filter 12, and the second electrode E2 is located on the bottom surface of the PCB 31.

In the present embodiment, the location of the first electrode E1 is not limited to be on the lower surface of the filter 12, and the location of the second electrode E2 is not limited to be on the lower surface of the PCB 31. For instance, the first electrode El may be located above the filter 12, and the second electrode E2 may be located between the PCB 31 and the concentration device 14 or on the fixture 30 below the PCB 31.

Figure 11D:
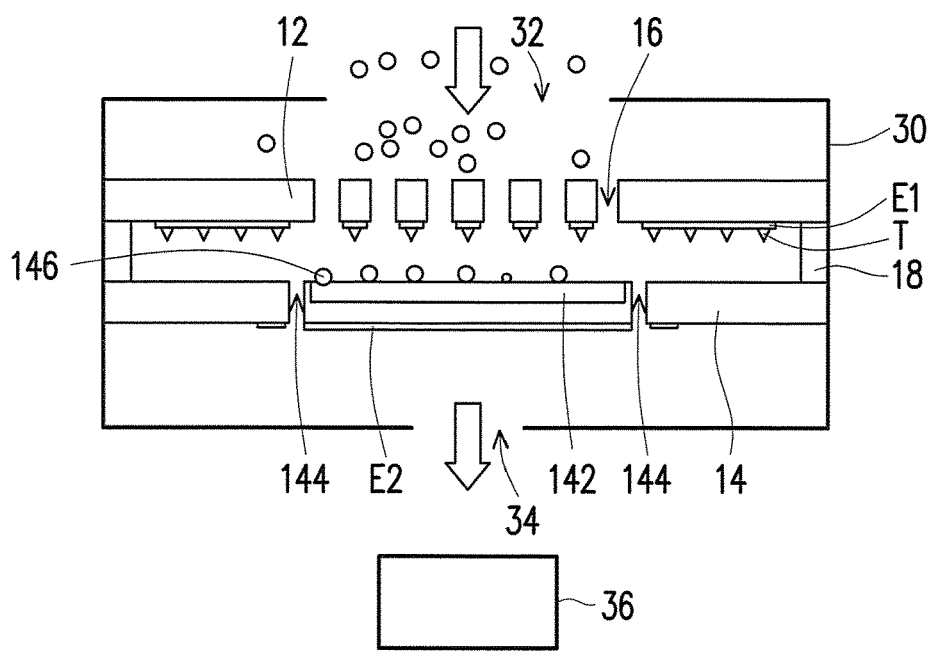
FIG. 11D is a cross-sectional schematic view of a miniaturized particulate matter detector according to a sixteenth exemplary embodiment.
Figure 11E:
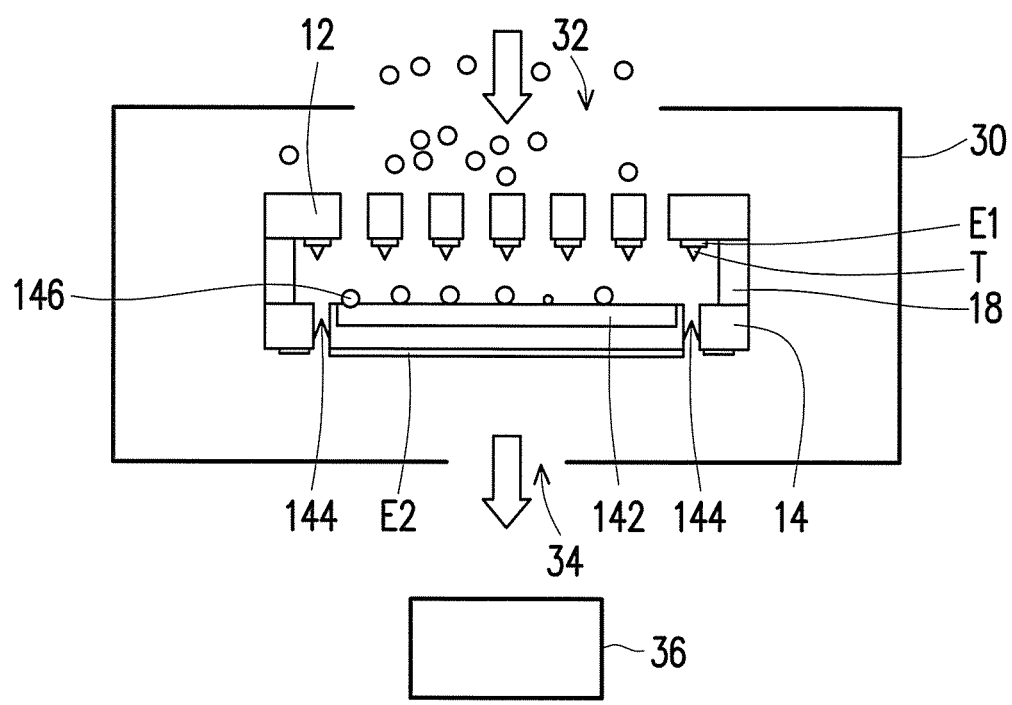
FIG. 11E is a cross-sectional schematic view of a miniaturized particulate matter detector according to a seventeenth exemplary embodiment.

FIG. 11D is a cross-sectional schematic view of a miniaturized particulate matter detector according to a sixteenth exemplary embodiment. FIG. 11E is a cross-sectional schematic view of a miniaturized particulate matter detector according to a seventeenth exemplary embodiment. With reference to FIG. 5D to FIG. 5E and FIG. 11D to FIG. 11E, the miniaturized particulate matter detector shown in FIG. 5D to FIG. 5E and provided in the present embodiment is similar to the miniaturized particulate matter detectors provided in the ninth embodiment to the tenth embodiment (FIG. 11D to FIG. 11E), while the differences therebetween are provided below. In the present embodiment, the miniaturized particulate matter detector further includes a first electrode E1 and a second electrode E2. The first electrode E1 has a plurality of discharge tips T pointing at the concentration detector 14, and the discharge tips T are suitable for charging the miniaturized particulate matter 146. Besides, as shown in FIG. 11D and 11E, in the present embodiment, the first electrode E1 is located on the lower surface of the filter 12, and the second electrode E2 is located on the bottom surface of the concentration detector 14.

In the present embodiment, the location of the first electrode E1 is not limited to be on the lower surface of the filter 12, and the location of the second electrode E2 is not limited to be on the lower surface of the concentration detector 14. For instance, the first electrode E1 may be located above the filter 12, and the second electrode E2 may be located on the fixture 30 below the concentration detector 14.

Figure 12A:
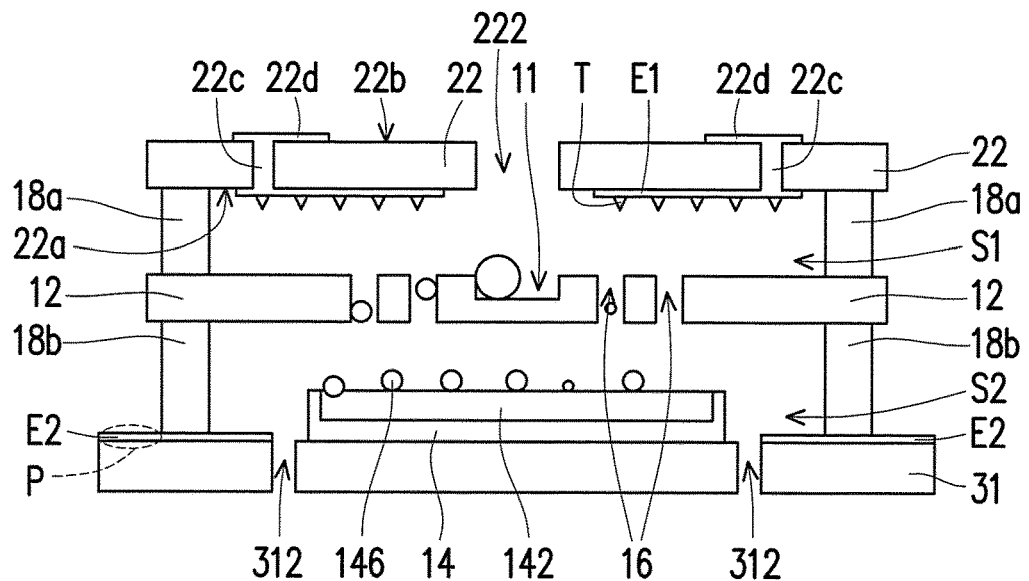
FIG. 12A to FIG. 12D are cross-sectional schematic views of a miniaturized particulate matter detector according to an eighteenth exemplary embodiment.
Figure 12B:
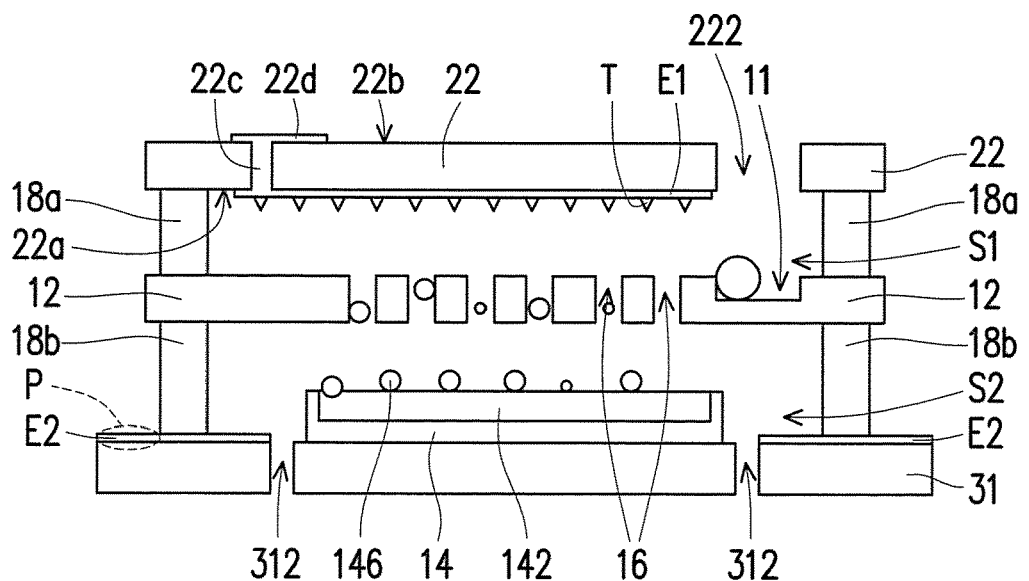

FIG. 12A to FIG. 12D are cross-sectional schematic views of a miniaturized particulate matter detector according to an eighteenth exemplary embodiment. With reference to FIG. 12A and FIG. 12B, the miniaturized particulate matter detector provided in the present embodiment includes a filter 12, a concentration detector 14, a first electrode E1, a second electrode E2, a top cover 22, and a printed circuit board (PCB) 31. The filter has a plurality of holes 16. The concentration detector 14 is correspondingly disposed under the filter 12, and the concentration detector 14 has a detect area 142. The first electrode E1 has a plurality of discharge tips T pointing at the concentration detector 14, and the discharge tips T are suitable for charging the miniaturized particulate matter. The concentration detector 14 is located between the first electrode E1 and the second electrode E2, and the first electrode E1 and the second electrode E2 are adapted to generate an electric field at least applied between the filter 12 and the concentration detector 14, so as to drive the charged miniaturized particulate matter 146 toward the concentration detector 14 from the filter 12, and the charged miniaturized particulate matter 146 is attached to the detect area 142 of the concentration detector 14. Additionally, the top cover 22 is located above the filter 12, the first electrode E1 is located on the top cover 22, and the first electrode E1 is located between the top cover 22 and the filter 12. The PCB 31 is configured to support the concentration detector 14, the second electrode E2 is located on the PCB 31 and between the PCB 31 and the concentration detector 14.

As shown in FIG. 12A and FIG. 12B, the top cover 22 has an inside surface 22a facing the filter 12, an outside surface 22b opposite to the inside surface 22a, a first conductive through-hole 22c, and a first pad 22d located on the outside surface 22b. The first electrode E1 is located on the inside surface 22a of the top cover 22, and the first electrode E1 is electrically connected to the first pad 22d through the conductive through-hole 22c. In the present embodiment, the number of the conductive through-hole 22c and the number of the first pad 22d may be modified according to actual design requirements. A first adhesive material 18a is disposed between the top cover 22 and the filter 12, for instance, so as to form a first space S1 between the top cover 22 and the filter 12. A second adhesive material 18b is disposed between the filter 12 and the PCB 31, for instance, so as to form a second space S2 between the filter 12 and the PCB 31. The first space S1 communicates with the second space S2 through the plurality of holes 16 of the filter 12.

In the present embodiment, the first and the second adhesive materials 18a and 18b are insulating adhesive materials or conductive adhesive materials, for instance, but the materials should not be limited as such.

With reference to FIG. 12A and FIG. 12B, the second electrode E2 arranged on the PCB 31 extends to the outside of the second space S2 from the inside of the second space S2, for instance, and the second electrode E2 has a second pad P located outside the second space S2. As schematically shown in FIG. 12A, proper voltages may be respectively applied to the first electrode E1 and the second electrode E2 through the first pad 22d and the second pad P, and the first pad 2d and the second pad P are at different horizontal levels.

Besides, the top cover 22 provided in the present embodiment has an air inlet 222, and the filter 12 has a collection groove 11 located under the air inlet 222, so as to collect particles with a diameter greater than a diameter of the plurality of holes 16. Thereby', the particles with the greater diameter are less likely to block the holes 16. As shown in FIG. 12A, the collection groove 11 corresponds to the central portion of the filter 12 and is distributed among the holes 16 of the filter 12, for instance, and the air inlet 222 corresponding to the collection groove 11 is located at the central portion of the top cover 22, for instance.

As shown in FIG. 12B, the collection groove 11 is located on edge portions or around corner portions of the filter 12. That is, the collection groove 11 is located on one side of the holes 16, and the air inlet 222 corresponding to the collection groove 11 is located on the edge portions or around the corner portions of the top cover 22, for instance.

Figure 12C:
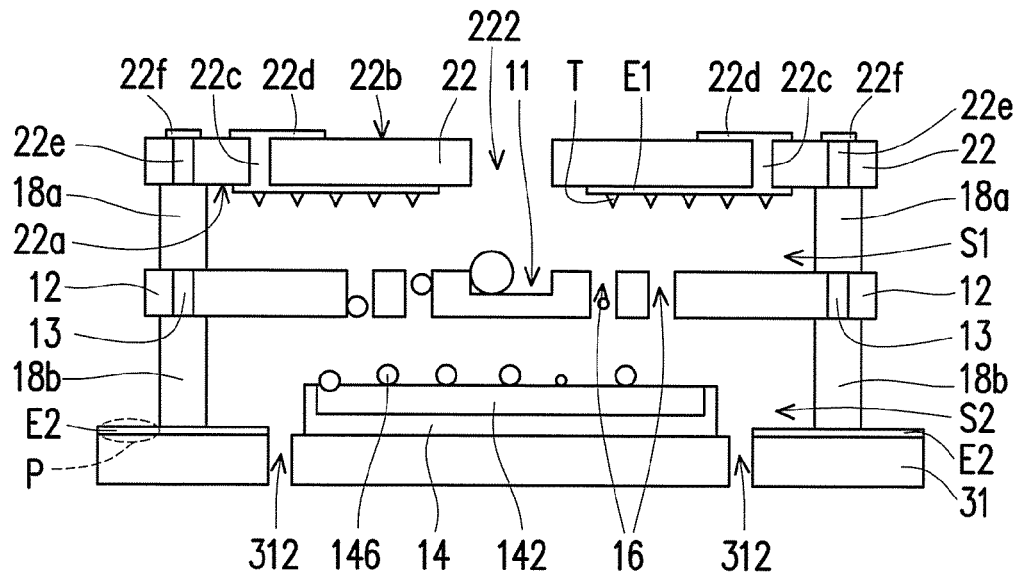
Figure 12D:
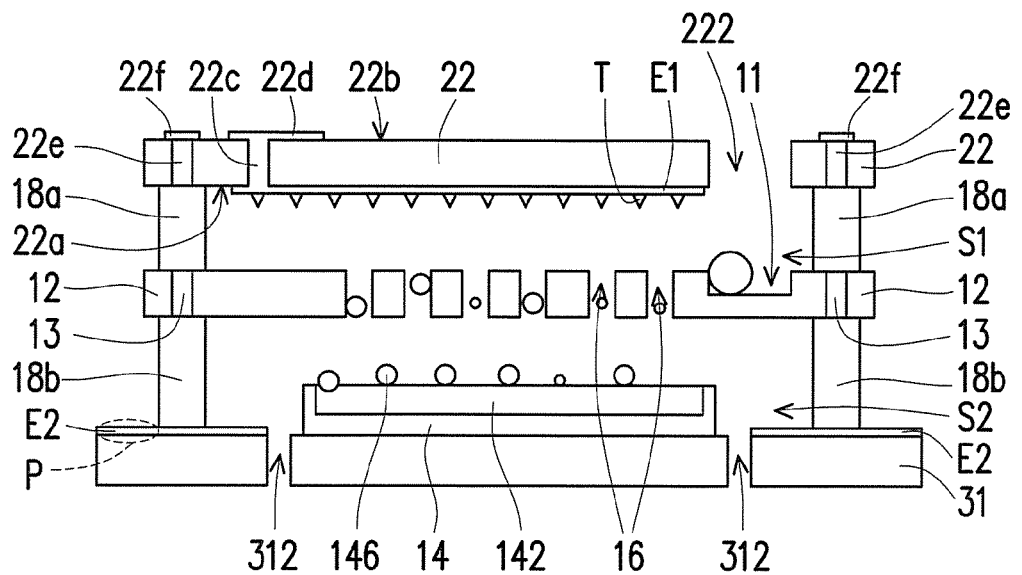

With reference to FIG. 12A to FIG. 12D, the miniaturized particulate matter detector shown in FIG. 12C to FIG. 12D is similar to the miniaturized particulate matter detector shown in FIG. 12A to FIG. 12B, while the differences therebetween are provided below. In the miniaturized particulate matter detector shown in FIG. 12C to FIG. 12D, the top cover 22 further includes a second conductive through-hole 22e and a second pad 22f located on the outside surface 22b, the filter 12 has at least one third conductive through-hole 13, the first adhesive material 18a and the second adhesive material 18b are conductive adhesive materials, and the second electrode E2 is electrically connected to the second pad 22f through the second adhesive material 18b, the third conductive through-hole 13, the first adhesive material 18a, and the second conductive through-hole 22e. With reference to FIG. 12C and FIG. 12D, it can be learned that the second pad 22f is electrically connected to the first adhesive material 18a through the second conductive through-hole 22e, the first adhesive material 18a is electrically connected to the second adhesive material 18b through the third conductive through-hole 13, and the second adhesive material 18b is located on and electrically connected to the second electrode E2.

As schematically shown in FIG. 12C and FIG. 12D, proper voltages may be respectively applied to the first electrode E1 and the second electrode E2 through the first pad 22d and the second pad 22f, and the first pad 22d and the second pad 22f are at the same horizontal level (i.e., on the outside surface 22b of the top cover 22).

In view of the above, the miniaturized particulate matter detector provided in the exemplary embodiments uses the developer and the etching scheme to make the TSV filter, and this may greatly reduce the selecting number of the opening size and the inlet sizes for detecting the miniaturized particulate matter. Arrangement of a modularized detector, for instance, a MEMS oscillator or a quartz oscillator may miniaturize these modules. The replaceable function allows the replacement of the filter that has no filtering function or the replacement of the detector that is supersaturated. Mass production and assembly in batch reduce the costs. Besides, modularized products may be applied in portable products, for example, cell phones.

Therefore, the disclosed exemplary embodiments of the disclosure may develop and achieve miniaturized modules for detecting miniaturized particulate matters. Also, the disclosed exemplary embodiments may widely be applied to portable products, widely monitoring, and so on. This may stay away from pollution of miniaturized particulate matters, find out the sources of causing the pollution, and reduce the chances that may cause lung cancer.

It will be apparent to those skilled in the art that various modifications and variations can be made to the disclosed embodiments of the disclosure. It is intended that the specification and examples be considered as exemplary embodiments only, with a scope of the disclosure being indicated by the following claims and their equivalents.

What is claimed is:

1. A miniaturized particulate matter detector comprising:
   a filter having a plurality of holes;
   a concentration detector correspondingly disposed under the filter, wherein the concentration detector has a detect area;
   a first electrode having a plurality of discharge tips pointing at the concentration detector, the plurality of discharge tips being suitable for charging the miniaturized particulate matter; and
   a second electrode, wherein the concentration detector is located between the first electrode and the second electrode, the first electrode and the second electrode are adapted to generate an electric field at least applied between the filter and the concentration detector, so as to drive the charged miniaturized particulate matter toward the concentration detector from the filter, and the charged miniaturized particulate matter is attached to the detect area of the concentration detector.

2. The miniaturized particulate matter detector of claim 1, wherein the filter is located between the first electrode and the concentration detector, the concentration detector is located between the second electrode and the filter, and the plurality of discharge tips point at the filter and the concentration detector, so as to charge the miniaturized particulate matter detector between the first electrode and the filter.

3. The miniaturized particulate matter detector of claim 2, further comprising:
   a top cover located above the filter, wherein the first electrode is located on the top cover, and the first electrode is located between the top cover and the filter; and
   a circuit board supporting the concentration detector, wherein the second electrode is located on the circuit board and between the circuit board and the concentration detector.

4. The miniaturized particulate matter detector of claim 3, wherein the top cover has an inside surface facing the filter, an outside surface opposite to the inside surface, a first conductive through-hole, and a first pad located on the outside surface, the first electrode is located on the inside surface of the top cover, and the first electrode is electrically connected to the first pad through the first conductive through-hole.

5. The miniaturized particulate matter detector of claim 4, wherein a first adhesive material is disposed between the top cover and the filter, so as to form a first space between the top cover and the filter, a second adhesive material is disposed between the filter and the circuit board, so as to form a second space between the filter and the circuit board, and the first space communicates with the second space through the plurality of holes of the filter.

6. The miniaturized particulate matter detector of claim 5, wherein the second electrode disposed on the circuit board extends to an outside of the second space from an inside of the second space, and the second electrode has a second pad located outside the second space.

7. The miniaturized particulate matter detector of claim 5, wherein the top cover further comprises a second conductive through-hole and a second pad located on the outside surface, the filter has a third conductive through-hole, the first adhesive material and the second adhesive material comprise conductive adhesive materials, and the second electrode is electrically connected to the second pad through the second adhesive material, the third conductive through-hole, the first adhesive material, and the second conductive through-hole.

8. The miniaturized particulate matter detector of claim 1, further comprising:

a top cover having an air inlet, wherein the filter is located between the top cover and the concentration detector, and the filter has a collection groove located under the air inlet, so as to collect particles with a diameter greater than a diameter of the plurality of holes;

a circuit board supporting the concentration detector and having at least one dielectric layer, wherein the circuit board has at least one air hole.

9. The miniaturized particulate matter detector of claim 8, wherein the collection groove is located on one side of the plurality of holes.

10. The miniaturized particulate matter detector of claim 8, wherein the collection groove is located among the plurality of holes.

11. The miniaturized particulate matter detector of claim 1, wherein the first electrode is located between the filter and the concentration detector, the concentration detector is located between the first electrode and the second electrode, and the plurality of discharge tips point at the concentration detector, so as to charge the miniaturized particulate matter detector between the first electrode and the concentration detector.

12. The miniaturized particulate matter detector of claim 11, further comprising:
   a first support plate having an upper surface and a lower surface, wherein the filter is located on the upper surface of the first support plate, and the first electrode is located on the lower surface of the first support plate.

13. The miniaturized particulate matter detector of claim 11, further comprising:
   a second support plate supporting the concentration detector, wherein the second electrode is located on the second support plate.

14. The miniaturized particulate matter detector of claim 1, wherein the plurality of discharge tips comprise conductive bumps with tips.

\* \* \* \* \*